(12) United States Patent
Bickford et al.

(10) Patent No.: US 11,327,102 B2
(45) Date of Patent: *May 10, 2022

(54) MINIATURE ELECTRIC FIELD DETECTOR

(71) Applicant: THE CHARLES STARK DRAPER LABORATORY, INC., Cambridge, MA (US)

(72) Inventors: James A. Bickford, Winchester, MA (US); Stephanie Lynne Golmon, Arlington, MA (US); Paul A. Ward, Dedham, MA (US); William D. Sawyer, Littleton, MA (US); Marc Steven Weinberg, Needham, MA (US); John J. Le Blanc, North Andover, MA (US); Louis Kratchman, Quincy, MA (US); James S. Pringle, Jr., Newton, MA (US); Daniel K. Freeman, Reading, MA (US); Amy Duwel, Cambridge, MA (US); Max Lindsay Turnquist, Somerville, MA (US); Ronald Steven McNabb, Jr., Charlestown, MA (US); William A. Lenk, Cambridge, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/001,899

(22) Filed: Aug. 25, 2020

(65) Prior Publication Data
US 2020/0386803 A1 Dec. 10, 2020

Related U.S. Application Data

(63) Continuation of application No. 15/944,106, filed on Apr. 3, 2018, now Pat. No. 10,859,620.
(Continued)

(51) Int. Cl.
*G01R 29/12* (2006.01)
*G01R 1/04* (2006.01)
(Continued)

(52) U.S. Cl.
CPC .............. *G01R 29/12* (2013.01); *A61B 5/24* (2021.01); *A61B 5/369* (2021.01); *G01R 1/04* (2013.01);
(Continued)

(58) Field of Classification Search
CPC ..... G01D 18/004; G01N 33/46; G01N 33/383
See application file for complete search history.

(56) References Cited

U.S. PATENT DOCUMENTS 4,380,735 A 4/1983 Bell
4,439,732 A 3/1984 Hesterman et al.
(Continued)

FOREIGN PATENT DOCUMENTS

CN 102879655 A 1/2013
CN 103390478 A 11/2013
(Continued)

OTHER PUBLICATIONS

Ando et al., "E-Field Ferroelectric Sensor: Modeling and Simulation", IEEE Instrumentation & Measurement Magazine, pp. 31-37, 2009.
(Continued)

*Primary Examiner* — Alvaro E Fortich
(74) *Attorney, Agent, or Firm* — Lando & Anastasi, LLP

(57) ABSTRACT

Aspects are generally directed to a compact and low-noise electric field detector, methods of operation, and methods of production thereof. In one example, an electric field detector includes a proof mass, a source of concentrated charge coupled to the proof mass, and a substrate having a substrate offset space defined therein, the proof mass being suspended
(Continued)

above the substrate offset space. The electric field detector further includes a sense electrode disposed on the substrate within the substrate offset space and proximate the proof mass, the sense electrode being configured to measure a change in capacitance relative to the proof mass from movement of the proof mass in response to a received electric field at the source of concentrated charge. The electric field detector includes a control circuit coupled to the sense electrode and configured to determine a characteristic of the electric field based on the measured change in capacitance.

22 Claims, 11 Drawing Sheets

Related U.S. Application Data

(60) Provisional application No. 62/481,322, filed on Apr. 4, 2017.

(51) Int. Cl.
| | |
|---|---|
| *G01R 33/12* | (2006.01) |
| *G01R 29/08* | (2006.01) |
| *G01R 27/26* | (2006.01) |
| *G01R 29/10* | (2006.01) |
| *A61B 5/24* | (2021.01) |
| *A61B 5/369* | (2021.01) |
| *A61B 5/318* | (2021.01) |

(52) U.S. Cl.
CPC ..... *G01R 27/2605* (2013.01); *G01R 29/0878* (2013.01); *G01R 29/105* (2013.01); *G01R 33/1261* (2013.01); *A61B 5/318* (2021.01); *A61B 2562/0214* (2013.01)

(56) References Cited

U.S. PATENT DOCUMENTS

| | | | |
|---|---|---|---|
| 4,600,883 | A | 7/1986 | Egli et al. |
| 4,670,092 | A | 6/1987 | Motamedi |
| 5,224,380 | A * | 7/1993 | Paik .......... G01P 15/18 73/510 |
| 5,908,986 | A | 6/1999 | Mitamura |
| 5,945,898 | A | 8/1999 | Judy et al. |
| 5,987,986 | A * | 11/1999 | Wyse .......... G01C 19/5719 73/504.12 |
| 6,028,773 | A | 2/2000 | Hundt |
| 6,250,156 | B1 | 6/2001 | Seshia et al. |
| 6,429,652 | B1 | 8/2002 | Allen et al. |
| 6,487,864 | B1 | 12/2002 | Platt et al. |
| 6,670,809 | B1 | 12/2003 | Edelstein et al. |
| 6,874,363 | B1 | 4/2005 | Foote et al. |
| 7,185,541 | B1 | 3/2007 | Edelstein |
| 7,231,094 | B2 | 6/2007 | Bickford et al. |
| 7,394,245 | B2 | 7/2008 | Brunson et al. |
| 7,642,692 | B1 | 1/2010 | Pulskamp |
| 7,773,228 | B1 | 8/2010 | Hollingsworth et al. |
| 7,972,888 | B1 | 7/2011 | Li et al. |
| 8,205,497 | B1 | 6/2012 | Okandan et al. |
| 8,674,689 | B1 | 3/2014 | Nielson et al. |
| 8,701,490 | B2 | 4/2014 | Jiang et al. |
| 9,182,454 | B1 | 11/2015 | Williams et al. |
| 10,531,805 | B2 | 1/2020 | Bickford et al. |
| 10,564,200 | B2 | 2/2020 | Bickford et al. |
| 10,585,150 | B2 | 3/2020 | Bickford et al. |
| 2002/0162947 | A1 | 11/2002 | Weitekamp et al. |
| 2003/0140699 | A1 | 7/2003 | Pike et al. |
| 2003/0200807 | A1 * | 10/2003 | Hulsing, II .......... G01P 15/125 73/514.01 |
| 2004/0187578 | A1 | 9/2004 | Malametz et al. |
| 2005/0234329 | A1 | 10/2005 | Kraus et al. |
| 2006/0032306 | A1 | 2/2006 | Robert |
| 2006/0283246 | A1 * | 12/2006 | Weinberg .......... G01C 19/5733 73/504.16 |
| 2007/0029629 | A1 * | 2/2007 | Yazdi .......... G01C 19/5719 73/514.32 |
| 2007/0096729 | A1 | 5/2007 | Brunson et al. |
| 2010/0005884 | A1 | 1/2010 | Weinberg et al. |
| 2010/0099942 | A1 | 4/2010 | Portelli |
| 2010/0108478 | A1 * | 5/2010 | Zhe .......... G01P 15/135 200/61.45 R |
| 2010/0295138 | A1 * | 11/2010 | Montanya Silvestre .......... B81C 1/00246 257/415 |
| 2011/0048133 | A1 | 3/2011 | Lin et al. |
| 2011/0054345 | A1 | 3/2011 | Nagatani |
| 2011/0056294 | A1 | 3/2011 | Simoni et al. |
| 2011/0062820 | A1 | 3/2011 | Aoyagi et al. |
| 2012/0272711 | A1 * | 11/2012 | Supino .......... G01C 25/005 73/1.38 |
| 2012/0326700 | A1 * | 12/2012 | Swanson .......... G01P 15/097 324/76.11 |
| 2013/0324832 | A1 | 12/2013 | Wu et al. |
| 2014/0023999 | A1 | 1/2014 | Greder |
| 2014/0125325 | A1 | 5/2014 | Ocak et al. |
| 2014/0182377 | A1 | 7/2014 | Lin et al. |
| 2014/0308757 | A1 | 10/2014 | Ju |
| 2014/0316188 | A1 | 10/2014 | Peterchev et al. |
| 2014/0358016 | A1 | 12/2014 | Shapira et al. |
| 2014/0375338 | A2 | 12/2014 | Chi et al. |
| 2015/0226762 | A1 | 8/2015 | Seshia et al. |
| 2016/0023002 | A1 | 1/2016 | Schulhauser et al. |
| 2016/0081577 | A1 | 3/2016 | Sridhar et al. |
| 2016/0116499 | A1 | 4/2016 | Thompson |
| 2016/0120432 | A1 | 5/2016 | Sridhar et al. |
| 2016/0341762 | A1 | 11/2016 | Waters et al. |
| 2016/0349283 | A1 | 12/2016 | Bramhavar et al. |
| 2017/0097382 | A1 | 4/2017 | Bickford et al. |
| 2017/0097394 | A1 | 4/2017 | Bickford et al. |
| 2017/0276697 | A1 | 9/2017 | Campsie et al. |
| 2017/0281086 | A1 | 10/2017 | Donaldson |
| 2018/0284175 | A1 | 10/2018 | Bickford et al. |
| 2018/0292470 | A1 | 10/2018 | Bickford et al. |
| 2020/0025840 | A1 | 1/2020 | Bickford |

FOREIGN PATENT DOCUMENTS

| | | |
|---|---|---|
| CN | 103342562 B | 2/2015 |
| CN | 104459351 A | 3/2015 |
| CN | 205620559 U | 10/2016 |
| CN | 106093605 A | 11/2016 |
| DE | 102014204721 A1 | 9/2015 |
| EP | 0702981 A1 | 3/1996 |
| EP | 2199741 A2 | 6/2010 |
| EP | 2466257 A1 | 6/2012 |
| JP | 2011136158 A | 7/2011 |
| WO | 02084315 A1 | 10/2002 |
| WO | 2012071545 A1 | 5/2012 |
| WO | 2014025353 A1 | 2/2014 |
| WO | 2014205356 A2 | 12/2014 |

OTHER PUBLICATIONS

Angelakis et al., "EEG Neurofeedback: A Brief Overview and an Example of Peak Alpha Frequency Training for Cognitive Enhancement in the Elderly", The Clinical Neuropsychologist, vol. 21, pp. 110-129, Feb. 16, 2007.

Ashrafulla, S., "EEG and MEG: functional brain imaging with high temporal resolution", Jun. 2013, <URL: https://hgp.usc.edu/files/2013/06/Syed_EEG_MEG.pdf>.

Bai et al., "A novel easy-driving and easy-signal-processing electrostatic field sensor based on piezoresistance and PET lever", Author Submitted Manuscript, pp. 1-15.

Basar et al., "A review of brain oscillations in cognitive disorders and the role of neurotransmitters", Brain Research, vol. 1235, pp. 172-193, Jul. 2, 2008.

(56) References Cited

OTHER PUBLICATIONS

Bernstein et al., "Low-Noise MEMS Vibration Sensor for Geophysical Applications," Journal of Microelectromechanical Systems, val. 8, No. 4, pp. 433-438, 2009.
Bickford, J. "Monitoring Brain Activity (E-Field Sensor)", Draper, accessed Oct. 31, 2016.
Bogue, R., "Plessey launches range of unique electric field sensors", Sensor Review, vol. 32, No. 3, pp. 194-198, 2012.
Budzynski et al., "Introduction to Quantitative EEG and Neurofeedback: Advanced Theory and Applications," 2nd ed., Elsevier (2009), chapters 1, 6, 8 and 16.
Chen et al. "MEM Electric Field Sensor using Force Deflection with Capacitance Interrogation", Power & Energy Society General Meeting. IEEE (2013).
Chen et al., "Micromachined ac/dc electric field sensor with modulated sensitivity", Sensors and Actuators, No. 245, pp. 76-84, Apr. 26, 2016.
Choi, K., "Electroencephalography (EEG) based neurofeedback training for brain-computer interface (BCI)", pp. 1-26, Sep. 2013.
Datskos et al., "Using Micro-Electro-Mechanical Systems (MEMS) as Small Antennas", IEEE, 2012.
Denison et al., "A Self-Resonant MEMS-Based Electrometer", IEEE Instrumentation and Measurement Technology Conference Proceedings, May 2007, pp. 1-5.
Dilella et al., "A Micromachined Magnetic-Field Sensor Based on an Electron Tunneling Displacement Transducer," Sensors and Actuators vol. 86, pp. 8-20, 2000.
Dong et al., "Push-Pull Mode Magnetostrictive/Piezoelectric Laminate Composite with an Enhanced Magnetoelectric Voltage Coefficient," Applied Physics Letters, vol. 87, p. 62502. 2005.
Gabrielson, T.B., "Mechanical-Thermal Noise in Micromachined Acoustic and Vibration Sensors", IEEE Transactions On Electron Devices, vol. 40, No. 5, pp. 903-909, May 1993.
Goel, M. "Electret sensors, filters and MEMS devices: New challenges in materials research", Current Science (2003) vol. 85, No. 4, pp. 443-453.
Grummett et al., "Measurement of neural signals from inexpensive, wireless and dry EEG systems", Physiological Measurement, vol. 36, pp. 1469-1484, 2015.
Heintzelman et al., "Characterization and Analysis of Electric-field Sensors", IEEE, Dec. 17, 2015.
Huang et al., "A novel high-sensitivity electrostatic biased electric field sensor", Journal of Micromechanics and Microengineering, vol. 25, pp. 1-9, Aug. 17, 2015.
International Search Report and Written Opinion in application No. PCT/US2018/025856 dated Jul. 30, 2018.
Kelly et al., "Progress Toward Forecasting of Space Weather Effects on UHF Satcom after Operation Anaconda", Space Weather, Sep. 12, 2014, doi: 10.1002/2014SW001081.
Kingsley et al., "Photrodes for physiological sensing", SPIE 5317, Optical Fibers and Sensors for Medical Applications IV, Jun. 2004.
Kuriyama et al. "Electrostatic Field Distribution Measurement Using Silicon Micro-mirror Array", IEEE International Symposium on Electromagnetic Compatibility (2012), pp. 351-356.
Kyynarainen et al., "A 3D Micromechanical Compass," Sensors and Actuators A, vol. 142, pp. 561-568. 2008.
Latorre et al., "Micromachined CMOS Magnetic Field Sensor with Ferromagnetic Actuation," Proceedings of SPIE, vol. 4019, 2000.
Miles et al., "Report on Non-Contact DC Electric Field Sensors", Jun. 23, 2009.
Niv, S., "Clinical efficacy and potential mechanisms of neurofeedback", Personality and Individual Differences, vol. 54, pp. 676-686, Jan. 24, 2013.
Othmer, S., "Neuromodulation technologies: An attempt at classification", Introduction to Quantitative EEG and Neurofeedback: Advanced Theory and Applications, second edition, pp. 1-27, 2009.
Petrov et al., "Electric Field Encephalography as a Tool for Functional Brain Research: A Modeling Study", PLoS ONE 8(7): e67692. doi: 10.1371/journal.pone.0067692.
Prance, H., "Sensor Developments for Electrophysiological Monitoring in Healthcare", Applied Biomedical Engineering, pp. 265-286, Aug. 2011.
Schalk et al., "Brain Sensors and Signals", A Practical Guide to Brain-Computer Interfacing with General-Purpose Software for Brain-Computer Interface Research, Data Acquisition, Stimulus Presentation, and Brain Monitoring, pp. 9-35, 2010.
Stikic et al., "Modeling temporal sequences of cognitive state changes based on a combination of EEG-engagement, EEG-workload, and heart rate metrics", Frontiers in Neuroscience, vol. 8, article 342, pp. 1-14, Nov. 2014.
Fatarchuk et al., "A MEMS DC Current Sensor Utilizing Neodymium Rare Earth Magnets," Additional Conferences (Device Packaging, HiTEC, HiTEN, & CICMT): Jan. 2014, vol. 2014, No. DPC, pp. 001046-001071.
Toney et al., "Detection of Energized Structures with an Electro-Optic Electric Field Sensor", IEEE, pp. 1364-1369, May 2014.
Vasquez et al., "Optically-Interrogated Zero-Power MEMS Magnetometer", Journal of Microelectromechanical Systems, vol. 16, No. 2, pp. 336-343, Apr. 2007.
Wickenden et al., "Polysilicon Xylophone Bar Magnetometers," SPIE vol. 3876, pp. 267-273. Sep. 1999.
Williams et al., "Vacuum Steered-Electron Electric-Field Sensor", Journal of Microelectromechanical Systems, pp. 1-10, Jan. 15, 2013.
Yang et al., "Ferromagnetic Micromechanical Magnetometer," Sensors and Actuators A, vol. 97-98, pp. 88-97, 2002.
Zhao et al., "Fabrication and Characterization of All-Thin-Film Magnetoelectric Sensors," Applied Physics Letters, vol. 94, p. 243507. 2009.

\* cited by examiner

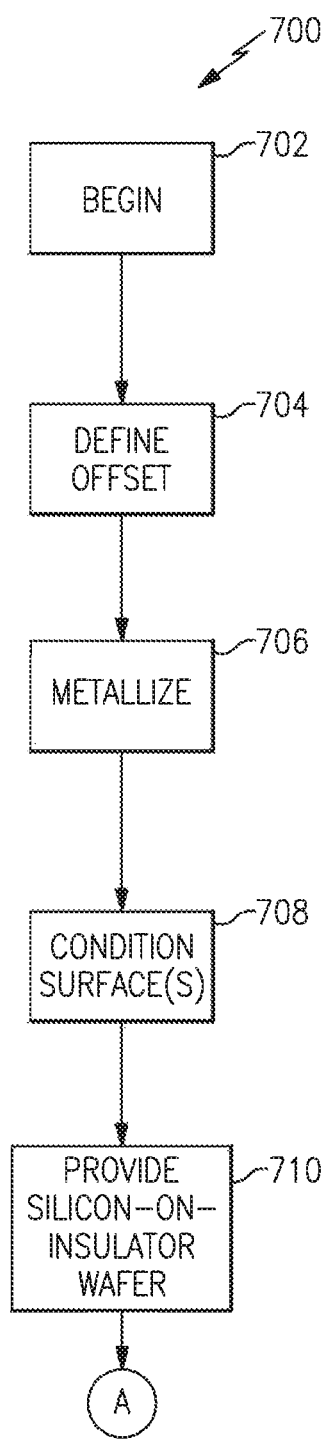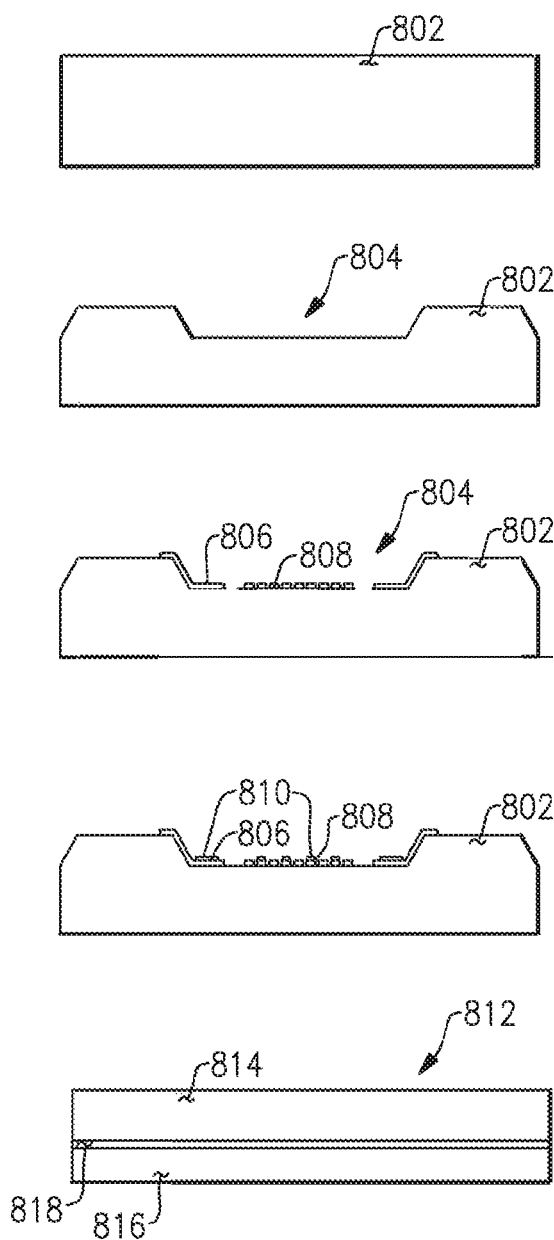
FIG.7A
FIG.8A

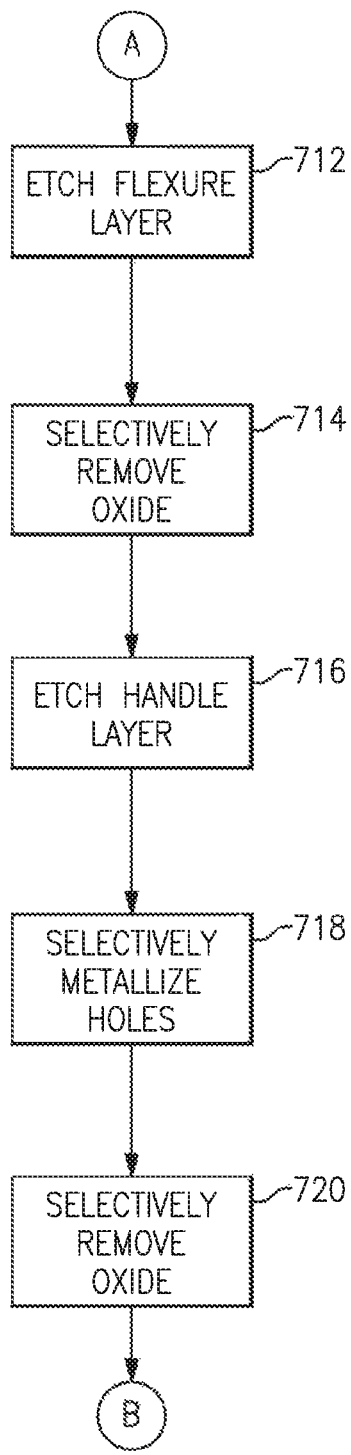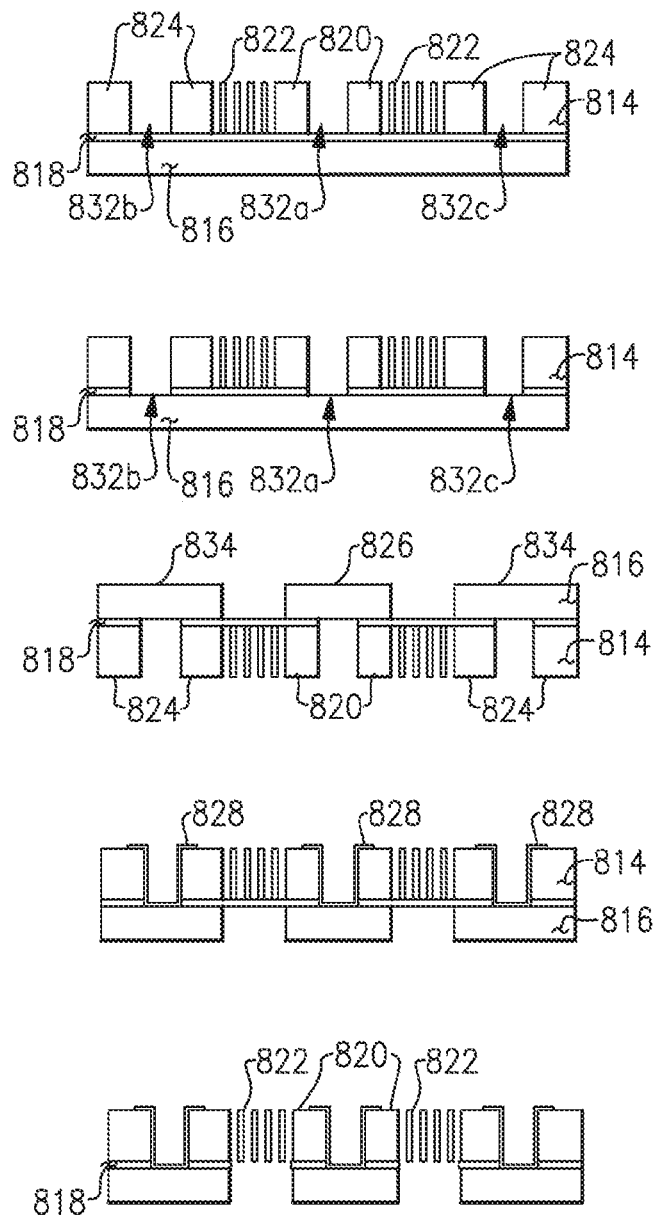
FIG.7B
FIG.8B

MINIATURE ELECTRIC FIELD DETECTOR

CROSS-REFERENCE TO RELATED APPLICATION

This application claims priority under 3 U.S.C. § 120 as a continuation of U.S. patent application Ser. No. 15/944,106, titled "MINIATURE ELECTRIC FIELD DETECTOR," filed on Apr. 3, 2018, which claims priority under 35 U.S.C. § 119(e) to U.S. Provisional Application Ser. No. 62/481,322, titled "MINIATURE ELECTRIC FIELD DETECTOR," filed on Apr. 4, 2017, each of which being incorporated herein by reference in its entirety.

BACKGROUND

The human body generates static and time-varying electromagnetic fields which may be measured and used in numerous applications. However, these fields are often faint, even in close proximity to the body, and attenuate as the distance from the human body is increased. For example, ionic currents within neurons of the brain will generate voltage fluctuations and magnetic fields during synaptic transmission. While these fields have proved challenging to accurately measure, some approaches exist for directly detecting the electrical activity produced by the body. Typically, numerous electrodes are arranged to measure voltages at a patient's scalp with electroencephalography (EEG), or highly sensitive magnetometers are employed during magnetocephalography (MEG) to detect magnetic fields. Other techniques, such as functional magnetic resonance imaging (f-MRI), are able to indirectly measure electrical activity via blood flow to relevant regions of the brain.

SUMMARY

Aspects and examples discussed herein are generally directed to a compact and low-noise electric field detector, methods of operation, and methods of production thereof. In particular, electric field detector designs disclosed herein may be incorporated within a contactless sensor array which is capable of detecting biophysical signals generated by the body of a patient or a user. In one example, the electric field detector is a microelectromechanical-based (MEMS-based) sensor which measures torsional motion of a suspended proof mass to determine one or more characteristics of a received electric field. Specifically, the electric field detector may include one or more capacitive sense electrodes which measure a variation in a charge between the proof mass and the sense electrode(s) as a result of the torsional motion of the proof mass in response to receiving the electric field. As further described below, particular examples may also include one or more flux concentrators, counterbalances, mechanical stop(s), and/or guard ring(s), which further improve the stability, robustness and noise performance of the electric field detector. Accordingly, aspects and examples discussed herein may achieve low-noise (e.g., less than 1 mV/m/rtHz at 10 Hz) performance at a compact size (e.g., less than 1 $cm^3$) and a low production cost.

According to certain examples, when incorporated within an array of similar electric field detectors, the embodiments described herein permit the use of electric field encephalography (EFEG) to directly measure electrical activity of the brain. In particular, the compact size and low production cost of each electric field detector improves upon existing diagnostic technologies which have been expensive to broadly utilize or are too difficult to practically implement in many important applications.

According to an aspect, provided is an electric field detector. In one example, the electric field detector comprises a proof mass, a source of concentrated charge coupled to the proof mass, a first sense electrode positioned proximate the proof mass and configured to measure a change in capacitance relative to the proof mass from movement of the proof mass in response to a received electric field at the source of concentrated charge, and a control circuit coupled to the first sense electrode and configured to determine a characteristic of the electric field based on the measured change in capacitance.

According to another aspect, provided is another electric field detector. In one example, the electric field detector comprises a proof mass, a source of concentrated charge coupled to the proof mass, a substrate having a substrate offset space defined therein, wherein the proof mass is suspended above the substrate offset space, a first sense electrode disposed on the substrate within the substrate offset space and positioned proximate the proof mass, the first sense electrode being configured to measure a change in capacitance relative to the proof mass from torsional movement of the proof mass in response to a received electric field at the source of concentrated charge, and a control circuit coupled to the first sense electrode and configured to determine a characteristic of the electric field based on the measured change in capacitance.

As further discussed herein, in some examples, the electric field detector further comprises a second sense electrode coupled to the control circuit. The second sense electrode may also be disposed on the substrate. In one example, the first sense electrode and the second sense electrode are configured to provide a differential capacitance measurement based on the change in capacitance from torsional movement of the proof mass. According to some examples, the electric field detector further comprises at least one support coupled to the proof mass and configured to suspend the proof mass above the substrate offset space.

According to at least one example, the electric field detector further comprises at least one drive electrode coupled to the control circuit and positioned proximate the proof mass, and the at least one drive electrode is configured to produce a feedback torque on the proof mass. In some examples, the at least one drive electrode is positioned on the substrate and within the substrate offset space. According to certain examples, the electric field detector further comprises a plurality of guard rings, each guard ring positioned to substantially surround a corresponding one of the first sense electrode or the at least one drive electrode.

According to various examples, the source of concentrated charge is configured to generate a static electric dipole. In one example, the source of concentrated charge is formed from a material configured to immobilize static charge, and may be an electret. In certain examples, the source of concentrated charge is a plurality of stacked electrets.

As further discussed herein, according to various examples the source of concentrated charge is configured to generate a dynamic electric dipole, the control circuit being configured to provide an induced voltage to vary the dynamic electric dipole. According to some examples, the electric field detector further comprises a counterbalance coupled to the proof mass, and the source of concentrated charge is coupled to a first surface of the proof mass and the counterbalance is coupled to a second distal surface of the proof mass. In some examples, the electric field detector further comprises at least one mechanical stop positioned to retain the proof mass within a predefined area of travel.

According to various examples, the electric field detector further comprises a structure wafer, and at least the proof mass and at least one support are defined in the structure wafer. In certain examples, the structure wafer is a Silicon-on-Insulator (SOI) wafer having a flexure layer, a handle layer, and an oxide layer interposed between the flexure layer and the handle layer, and the proof mass and the at least one support are defined in the flexure layer. In some examples, the electric field detector further comprises one or more counterbalances defined in the handle layer. In at least these examples, the structure wafer includes one or more plated holes through the oxide layer, and the one or more plated holes electrically couple the one or more counterbalances to the flexure layer.

In various examples, the electric field detector further comprises a levitation suspension system configured to levitate the proof mass relative to the substrate. The levitation suspension system may include at least one levitation forcer positioned proximate the proof mass and configured to apply a force to maintain the proof mass at a null point, and the at least one levitation forcer may be an electrostatic forcer or a magnetic forcer.

In various examples, the electric field detector further comprises a housing configured to enclose at least the proof mass, the first sense electrode, and the source of concentrated charge and provide a vacuum environment. According to certain examples, the electric field detector further comprises an auxiliary sensor coupled to the control circuit and configured to measure an external parameter, the external parameter including at least one of noise, a vibration, and an ambient temperature, and wherein the control circuit is configured to adjust the characteristic of the electric field to compensate for an effect of the measured external parameter on the characteristic of the electric field.

According to various examples, in determining the characteristic of the electric field the control circuit is configured to determine at least a direction (or directions) of the electric field. In certain examples, the electric field detector further comprises a substrate having a substrate offset space defined therein, the proof mass is suspended above the substrate offset space. In at least these examples, the electric field detector further comprises a second sense electrode disposed on the substrate and within the substrate offset space, and the control circuit includes a low-noise differential sine-wave carrier generator coupled to the first sense electrode and the second sense electrode and configured to excite the first sense electrode and the second sense electrode to increase a frequency of an electronics signal produced by the received electric field.

In various examples, the control circuit further includes a preamplifier coupled to the first sense electrode and the second sense electrode, the preamplifier configured to provide a carrier signal amplitude-modulated by the electric field. In at least one example, the control circuit further includes a demodulator and a baseband filter coupled to the demodulator, the demodulator being configured to receive the amplitude-modulated carrier signal, and the baseband filter being configured to extract the characteristic of the electric field from an output of the demodulator. According to various examples, control circuit is further configured to apply a bias voltage to the electric field detector to create a negative spring force on the proof mass. In at least one example, the control circuit is further configured to apply a feedback voltage to the first sense electrode to rebalance a position of the proof mass.

According to another aspect, provided is an electric field transduction method. In one example, the method comprises generating an electric charge distribution on a proof mass, measuring a change in capacitance between a sense electrode and the proof mass from torsional movement of the proof mass in response to receiving an electric field at the proof mass, and determining a characteristic of the electric field based on the measured change in capacitance.

According to another aspect, provide is another electric field transduction method. In one example, the electric field transduction method includes generating an electric charge distribution on a proof mass, the proof mass being suspended above a substrate offset space in a substrate relative to a first sense electrode disposed on the substrate, measuring a change in capacitance between the first sense electrode and the proof mass from torsional movement of the proof mass in response to receiving an electric field at the proof mass, and determining a characteristic of the electric field based on the measured change in capacitance.

According to various examples, the method further comprises providing a differential capacitance measurement from the first sense electrode and a second sense electrode based on the change in capacitance from the torsional movement of the proof mass. In some examples, the method further comprises suspending the proof mass relative to the sense electrode with at least one of one or more supports, one or more rotational bearings, an electrostatic suspension, or a magnetic suspension.

In various examples, the method further comprises providing a feedback torque on the proof mass with one or more drive electrodes positioned proximate the proof mass. In at least one example, generating the electric charge distribution on the proof mass includes forming a static electric dipole with an electret. In certain examples, the electric charge distribution on the proof mass is one of a static or dynamic electric dipole formed by a Piezo-electric material or an induced voltage on one or more electrodes proximate the proof mass.

According to various examples, the method further comprises counterbalancing the proof mass with a counterbalance coupled to the proof mass. In certain examples, the method further comprises measuring at least one of internal noise, external noise, an external vibration, and an ambient temperature, and correcting the characteristic of the electric field to compensate for the at least one of the internal noise, external noise, the external vibration, and the ambient temperature.

In certain examples, determining the characteristic of the electric field includes determining at least a direction, or multiple directions, of the electric field. According to various examples, the method further comprises exciting the first sense electrode and a second sense electrode with a low-noise differential sine-wave carrier generator coupled to the first sense electrode and the second sense electrode to increase a frequency of an electronics signal produced by the received electric field. In at least one example, exciting the first sense electrode and the second sense electrode with a low-noise differential sine-wave carrier generator includes generating and applying a carrier signal to the first sense electrode and the second sense electrode. In some examples, the method further comprises amplitude modulating the carrier signal with electric field information of the received electric field to generate an amplitude-modulated carrier signal, and demodulating the amplitude-modulated carrier signal and extracting the characteristic of the electric field from the demodulated carrier signal.

According to various examples, the method further comprises applying a bias voltage to create a negative spring force on the proof mass. In certain examples, the method further comprises applying a feedback voltage to the first sense electrode to rebalance a position of the proof mass.

According to an aspect, provided is a method for fabricating an electric field detector. In one example, the method comprises defining at least one substrate offset space in a substrate wafer, forming a first sense electrode on the substrate wafer and within the substrate offset space, defining a proof mass and at least one support in a structure wafer and suspending the proof mass by the at least one support to allow torsional movement of the proof mass, providing a source of concentrated charge on the proof mass, and coupling the substrate wafer and the structure wafer to position the proof mass proximate the substrate offset space of the substrate wafer and within capacitive communication with at least the first sense electrode.

According to various examples, the method further comprises providing the structure wafer, and the structure wafer includes a flexure layer, a handle layer, and an oxide layer interposed between the flexure layer and the handle layer. In at least one example, defining the proof mass and the at least one support in the structure wafer includes etching the flexure layer to form the proof mass and the at least one support. In some examples, the method further comprises selectively removing a first portion of the oxide layer exposed through the flexure layer. In at least one example, the method further comprises defining one or more counterbalances in the handle layer. In some examples, the method further comprises applying a metallic layer to one or more holes defined in the flexure layer to electrically couple the flexure layer and the handle layer of the structure wafer. In at least one example, the method further comprises selectively removing a second portion of the oxide layer exposed through the handle layer.

In various examples, the method further comprises applying one or more metallic bumps to a surface of the first sense electrode. According to various examples, the method further comprises forming a second sense electrode, a first drive electrode, and a second drive electrode on the substrate wafer and within the substrate offset space. In certain examples, forming the first sense electrode, the second sense electrode, the first drive electrode, and the second drive electrode on the baseplate wafer includes depositing a conducting material on a surface of the substrate wafer.

According to certain examples, providing the source of concentrated charge on the proof mass includes providing the source of concentrated charge on the proof mass within a vacuum environment. In certain examples, the method further comprises varying an electric dipole formed from the source of concentrated charge via an active excitation signal.

According to another aspect, provided is another electric field detector. In one example, the electric field detector comprises a proof mass, a source of concentrated charge coupled to the proof mass, a first sense electrode configured to measure a change in capacitance relative to the proof mass from torsional movement of the proof mass in response to a received electric field, a levitation suspension system configured to levitate the proof mass relative to the substrate, and a control circuit coupled to the first sense electrode and configured to determine a characteristic of the electric field based on the measured change in capacitance.

In various examples, the levitation suspension system includes at least one levitation forcer positioned proximate the proof mass and configured to apply a force to maintain the proof mass at a null point. According to certain examples, the at least one levitation forcer is one of an electrostatic forcer and a magnetic forcer.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with at least one of the objectives, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. Various aspects, embodiments, and implementations discussed herein may include means for performing any of the recited features or functions.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures:

FIG. 7A-7C is a process flow for fabricating an electric field detector, according to examples discussed herein;

FIGS. 8A-8C show a state of an electric field detector during each act of the process flow of FIG. 7A-7C, according to examples discussed herein;

DETAILED DESCRIPTION

Aspects and embodiments are generally directed to detectors for exploiting the electric component of electromagnetic signals. Particular examples may include an electric field detector capable of detecting bio-physical signals generated by the body of a patient or user, such as the electric field of his or her brain, heart, nerves, or muscles. Other examples of the electric field detector described herein may be suitable for detecting other weak electromagnetic signals.

In one example, the electric field detector is a microelectromechanical-based (MEMS-based) electric field detector which measures a torque on a suspended proof mass to determine one or more characteristics of a received electric field. In particular, an electric dipole is generated on the proof mass by placing a quasi-permanently charged material, such as a polymer electret, on the proof mass. The induced electric dipole generates a torque on the proof mass when exposed to an external electric field. The torque induces torsional motion in the proof mass, which causes a capacitance between one or more sense electrodes and the proof mass to change. The change in capacitance may then be measured to estimate one or more characteristics of the external electric field, such as a direction, phase, and/or a magnitude.

Figure 1:
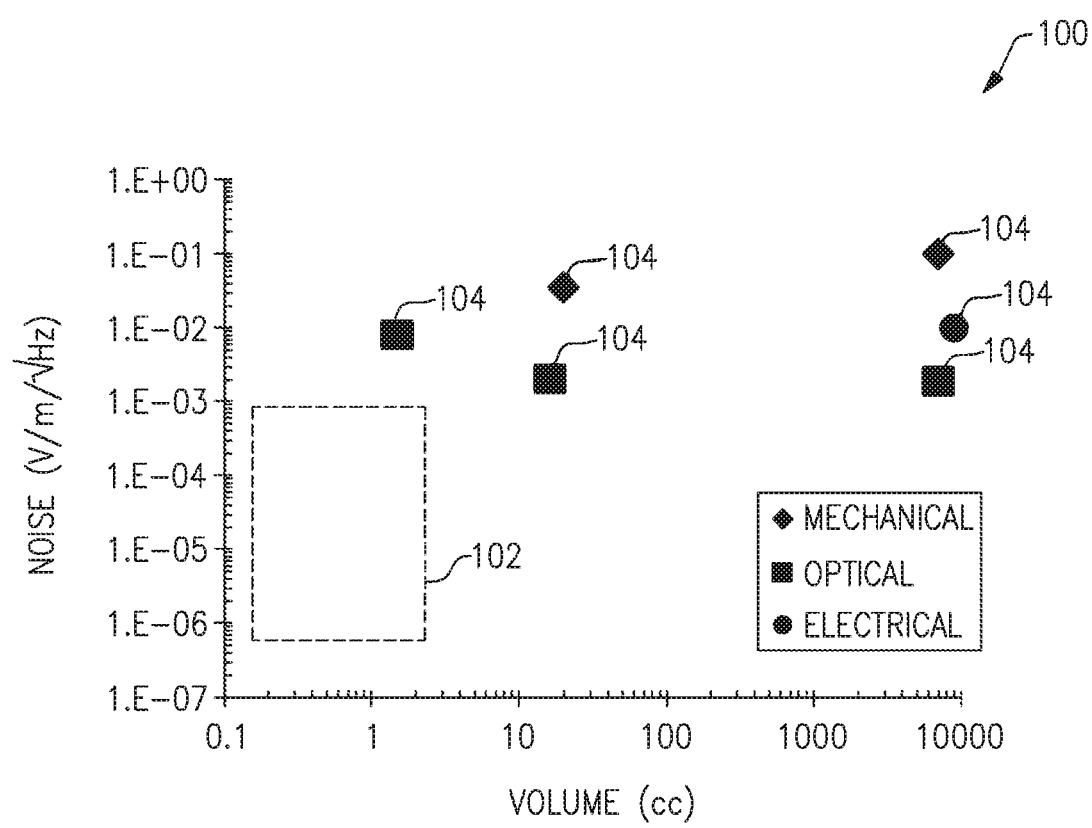
FIG. 1 is a chart showing examples of performance requirements for a compact electric field detector.

Various sources have discussed the use of Electric Field Encephalography (EFEG) to estimate brain activity. In particular, some literature has estimated a strength of the relevant bio-electrical signals generated by the brain. Based on the estimated strength of the relevant signals, the performance requirements for an electric field detector capable of detecting these bio-electrical signals can be determined. FIG. 1 illustrates a graph 100 of an example of the performance requirements (e.g., noise performance versus volume) for one such electric field detector. In particular, FIG. 1 illustrates these performance requirements (e.g., area 102) relative to the performance capabilities of currently available technology (e.g. points 104). FIG. 1 illustrates that the predicted signal magnitudes of the relevant bio-electrical signals are below the noise floor of current electric field sensors (e.g., mechanical, optical, and electrical-based sensors) that could be made compact and inexpensive enough for use in diagnostic applications.

Accordingly, various aspects and examples discussed herein are capable of meeting the performance requirements 102 illustrated in FIG. 1. That is, the electric field detector described herein is capable of directly measuring bio-electrical signals, such as brain activity, with an improvement in signal-to-noise ratio and volume. In some instances, the electric field detector is capable of meeting these performance requirements without contacting the head or body of the given patient or user. Such a design offers the benefit of improved user comfort and convenience. While described herein primarily in the context of bio-electrical signals, it is appreciated that various examples of the electric field detector described herein may also offer significant advantages in other areas of electric field detection.

It is to be appreciated that examples and/or embodiments of the apparatus and methods discussed herein are not limited in application to the details of construction and the arrangement of components set forth in the following description or illustrated in the accompanying drawings. The apparatus and methods are capable of implementation in other embodiments and of being practiced or of being carried out in various ways. Examples of specific implementations are provided herein for illustrative purposes only and are not intended to be limiting. In particular, acts, elements and features discussed in connection with any one or more examples and embodiments are not intended to be excluded from a similar role in any other example or embodiment. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, above and below, and vertical and horizontal are intended for convenience of description, not to limit the present systems and methods or their components to any one positional or spatial orientation.

The accompanying drawings are included to provide illustration and a further understanding of the various aspects and examples, and are incorporated in and constitute a part of this disclosure. The drawings, together with the remainder of the disclosure, serve to explain principles and operations of the described and claimed aspects and examples.

Figure 2A:
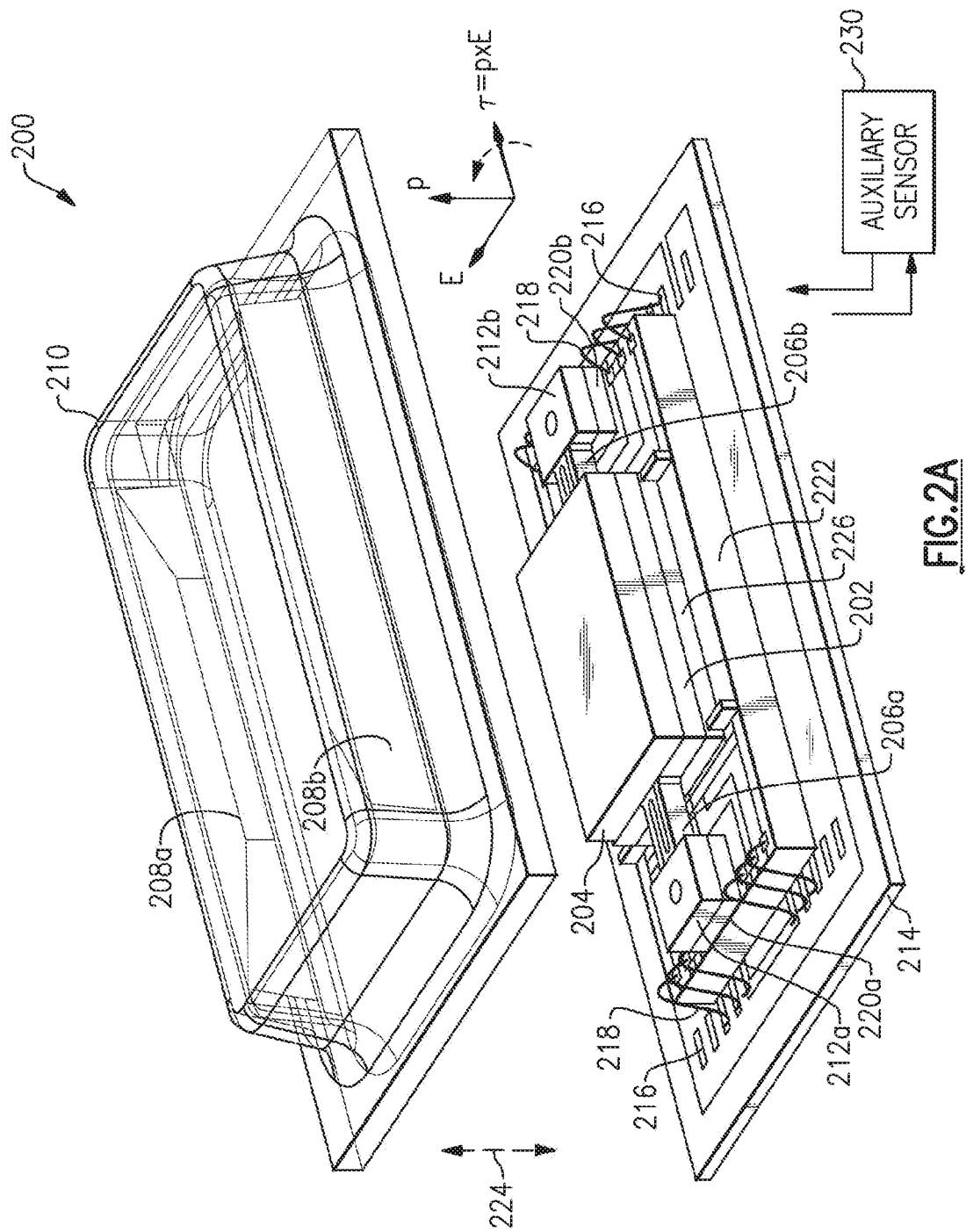
FIG. 2A is a perspective view of an electric field detector, shown with a housing detached from the detector, according to examples discussed herein.
Figure 2B:
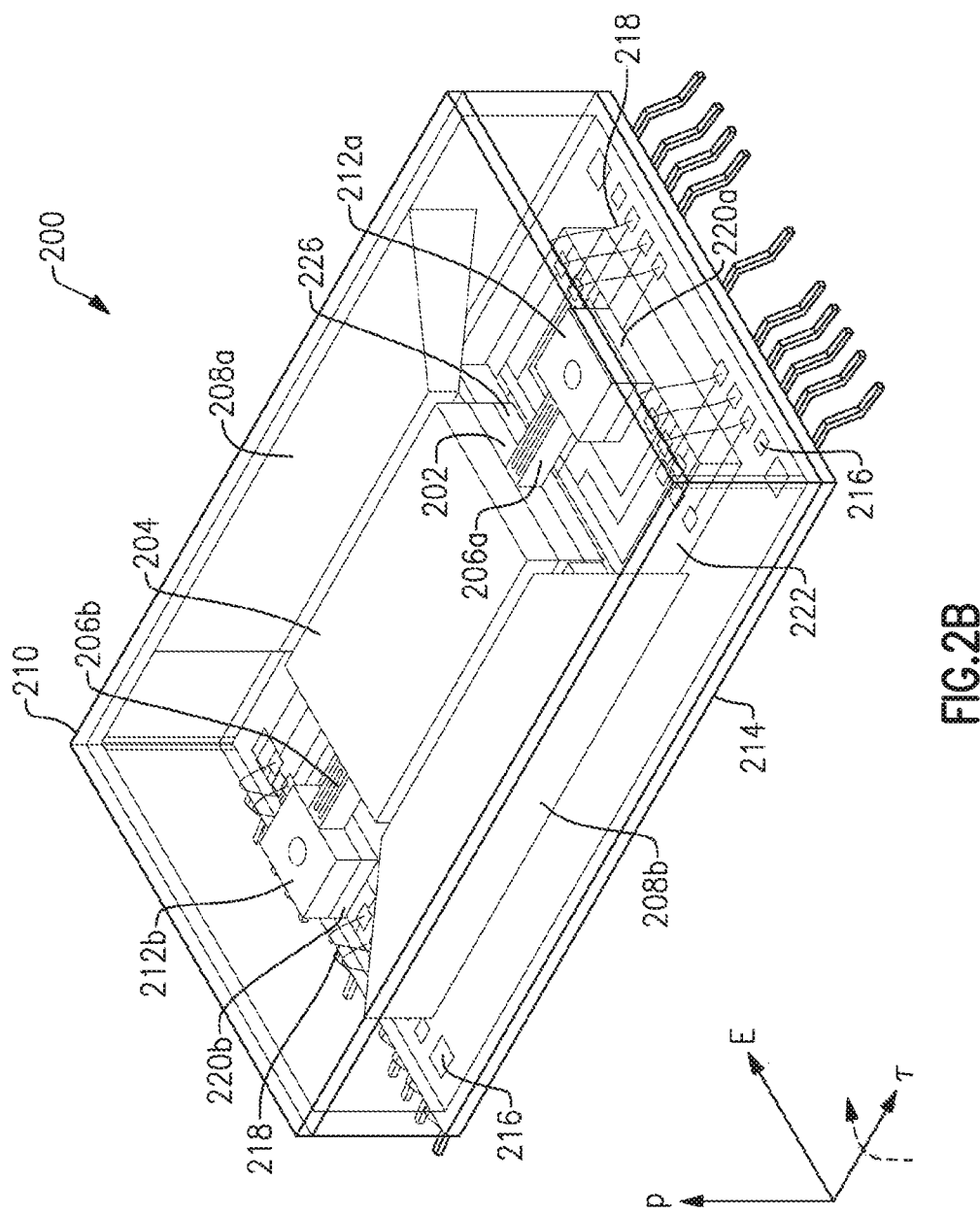
FIG. 2B is perspective view of the electric field detector illustrated in FIG. 2A with the housing attached, according to examples discussed herein.

FIGS. 2A and 2B each illustrate a perspective view of an electric field detector 200 according to various examples described herein. FIG. 2A illustrates a view of the detector 200 with a housing 210 detached from the detector 200, and FIG. 2B shows a view of the detector 200 with the housing 210 attached. The housing 210 may be removed in a vertical direction away from the detector 200 (e.g., direction 224), as shown in FIG. 2A. In FIGS. 2A and 2B, the electric field detector 200 includes a microelectromechanical-based (MEMS-based) resonator, which may be defined by processing a structure wafer (e.g., a Silicon-on-Insulator wafer) to a desired geometry. As shown, the detector 200 may include a proof mass 202 coupled to a source of concentrated charge 204, a plurality of supports 206a, 206b (collectively "supports 206"), one or more flux concentrators 208a, 208b (collectively "flux concentrators 208"), a housing 210, one or more anchors 212a, 212b (collectively "anchors 212"), a baseplate 214, one or more electrical contacts 216, one or more leads 218, and a substrate 222, among other components. While not shown in FIGS. 2A and 2B, each of the contacts 216 may couple the electric field detector 200 to a control circuit, examples of which are further discussed herein. In certain examples, the structure wafer is processed (e.g., etched) to define the proof mass 202, the plurality of supports 206, and the one or more anchors 212. In further examples, the electric field detector 200 may also include one or more counterbalances 226 that are coupled to the proof mass 202. In certain examples, the electric field detector 200 may also include one or more sense electrodes and one or more drive electrodes, each of which are positioned on the substrate 222 and obscured in FIGS. 2A and 2B by the counterbalance 226. As shown, the substrate 222 is positioned on the baseplate 214

In various examples, the electric field detector 200 determines one or more characteristics of a received electric field, which one instance is a bio-electrical signal, based on measured capacitance variations due to torsional motion of the proof mass 202 in response to receiving the electric field. While in some examples, a combination of linear forces may result in the torsional motion of the proof mass 202, in certain other examples, a variation in capacitance as a result of a single linear force may be measured. The proof mass 202 is supported by the plurality of supports 206, each of which form a rotationally compliant spring anchored to the substrate 222 via a respective anchor 212a, 212b. In the shown example, each support 206 is a flexured beam interposed between a side surface of the proof mass 202 and a corresponding anchor 212a, 212b. That is, a first support 206a is interposed between a first side surface of the proof mass 202 and a first anchor 212a, and a second support 206b is interposed between a second side surface of the proof mass 202 and a second anchor 212b. Each anchor is coupled to the substrate 222 with a respective anchor ground 220a, 220b. The first anchor 212a is coupled to the substrate 222 at the first anchor ground 220a, and the second anchor 212b is coupled to the substrate 22 at the second anchor ground 220b.

As shown in FIG. 2A, the first support 206a and the second support 206b may be coupled to opposing sides of the proof mass 202. The dimensions of the supports 206 are selected such that the overall stiffness of the supports 206 are sufficient to withstand operational shock loads while maximizing a response to input torques. While shown as including a pair of supports 206a, 206b, in various other examples the electric field detector may include one (e.g., in a "lever" arrangement) or any number of supports 206. For instance, the detector 200 may include three supports 206, or an arrangement of four or more supports 206.

In various other examples, the proof mass 202 may be levitated by an electrostatic suspension, levitated by an electromagnetic suspension, and/or suspended by an equivalent rotational bearing. Unlike the example illustrated in FIG. 2A, in these examples it may be advantageous to design the proof mass 202 (and/or source of concentrated charge 204) to have a circular or cylindrical shape to permit rotation thereof. In such an example, the levitated proof mass (e.g., relative to a substrate) is positioned to move (e.g., rotate) with very low resistance and low stiffness. Such an arrangement may maximize a scale factor of the electric field detector 200 while retaining a structural stability and robustness. In such an example, the electrostatic suspension, electromagnetic suspension, and/or rotational bearing may supplement the one or more illustrated flexured beams of FIG. 1 (e.g., supports 206) or replace the one or more flexured beams.

Figure 9:
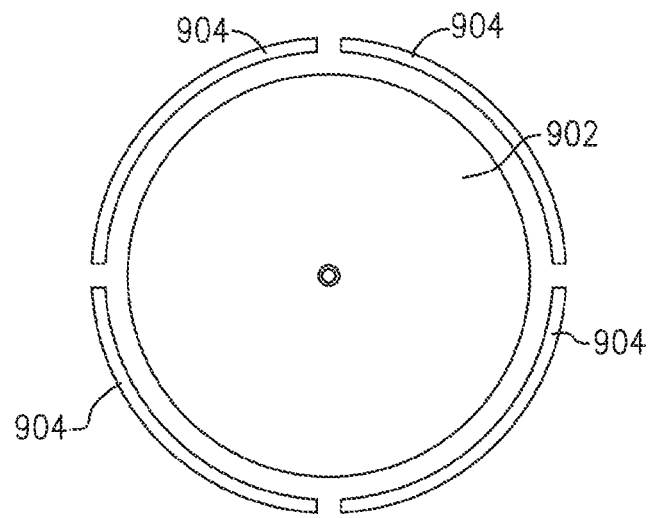
FIG. 9 is an axial view of a proof mass and levitation forcers, according to various examples discussed herein.
Figure 10:
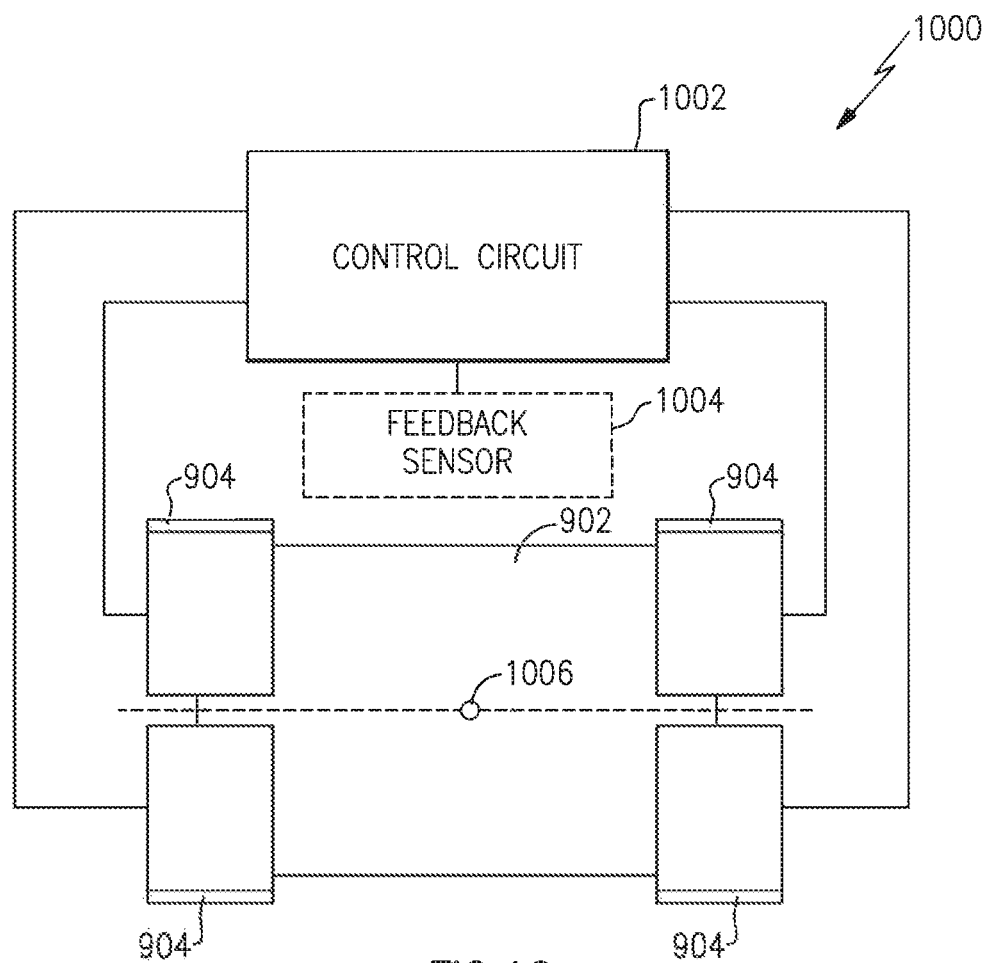
FIG. 10 is a side profile view of a levitation suspension system including the levitation forcers of FIG. 9, according to various examples discussed herein.

One example of a levitation suspension system 1000 is described with reference to FIG. 9 and FIG. 10. In particular, FIG. 9 illustrates an axial view of a proof mass 902 and levitation forcers 904, and FIG. 10 illustrates a profile view of a levitation suspension system 1000 that includes the levitation forcers 904 of FIG. 9. Examples of the levitation suspension system 1000 may be incorporated within any of the examples of the electric field detectors described herein, such as the electric field detector 200 described with reference to FIG. 2A and FIG. 2B. That is, the proof mass 902 may be the proof mass 202 illustrated in FIG. 1. FIG. 9 illustrates an axial view of a proof mass 902 and levitation forcers 904, and FIG. 10 shows a side profile view of the levitation suspension system 1000. As shown, the levitation suspension system 1000 may include one or more levitation forcers 904 that apply a levitating force to the proof mass 902 to levitate the proof mass against gravity and other induced forces. In certain examples, each of the one or more levitation forcers 904 may include one or more of the sense electrodes 502 or drive electrodes 504 further described below with reference to FIG. 5. While in certain examples, each levitation forcer 904 may be an electrostatic forcer (e.g., for electrostatic levitation), in various other examples, each levitation forcer 904 may be a magnetic forcer (e.g., for magnetic levitation).

A control circuit 1002 (e.g., control circuit 600 illustrated in FIG. 6) coupled to the levitation forcers 904 receives feedback from each levitation forcer 904 and/or one or more feedback sensors 1004. If a position of the proof mass 902 is displaced relative to a desired null point (e.g., shown as point 1006), the control circuit 1002 provides a control signal to one or more of the levitation forcers 904 to increase or decrease the force applied by the receiving levitation forcer 904 and return the proof mass 902 to the null position. In certain examples, the proof mass 902 may be metalized (e.g., at an end of the proof mass) to increase the sensitivity of the proof mass 902 to the levitation force. The position of the proof mass 902 (relative to the null position) may be capacitively measured based on a capacitance between the proof mass 902 and one or more sense electrodes (e.g., sense electrodes 502 described with reference to FIG. 5).

The number and arrangement of levitation forcers 904 may be selected based on the desired application of the corresponding electric field detector. While FIG. 9 illustrates a plurality of levitation forcers 904 (e.g., four) radially aligned about the circumference of an axial proof mass 902, various other arrangements are possible. In particular, the number, shape, and arrangement of levitation forcers 904 may depend on the particular shape of the proof mass 902 and packaging constraints (e.g., size, weight, available space, etc.). In addition to maintaining the proof mass 902 a desired null position, in certain instances, the levitation forcers 904 may be used to rotate the proof mass 902 at a desired velocity, or reposition the proof mass 902 to a desired orientation. In addition to assessing the position of the proof mass 902 relative to a null position, one or more signals from the illustrated feedback sensor 1004 may be used by the control circuit 1002 to infer external stimuli that induce proof mass 902 movement. The feedback sensor 1004 may be an optical sensor, an accelerometer, a capacitive sensor, or any other type of position sensor.

Referring to FIGS. 2A and 2B, in various examples, the plurality of supports 206 may suspend the proof mass 202 above a substrate offset space defined in the substrate 222. That is, the substrate 222 may include an area (referred to as a "substrate offset space") formed in a surface thereof beneath the proof mass 202 (e.g., and counterbalance 226 shown in FIGS. 2A and 2B). The substrate offset space is obscured in FIGS. 2A and 2B by the counterbalance 226. While described as being suspended "above" the substrate offset space, in other examples, the proof mass 222 may be partially positioned within the substrate offset space. In other examples, the proof mass 202 may be positioned in close proximity to the substrate offset space but not directly above the substrate offset space. As discussed, in certain examples, the electric field detector 200 may include one or more sense electrodes and one or more drive electrodes, each of which are positioned on the substrate 222 and in capacitive communication with the proof mass 202. In particular, each of the sense electrodes and the drive electrodes may be positioned within the substrate offset space and may form a sense gap with the proof mass 202. In certain examples, the substrate offset space is formed by etching the substrate 222; however, other processing techniques may be used to form the substrate offset space, such as milling, grinding, or one or more deposition processes. Various aspects of a substrate, a substrate offset space, sense electrodes, and drive electrodes are discussed below with reference to at least FIGS. 7A-7C and FIGS. 8A-8C.

In various examples an impinging electric field concentrated on the source of concentrated charge 204 generates a torque and effects motion of the proof mass 202. For instance, the torque, $\tau$, may be represented as:

$$\tau = p \times E$$

where, p, is the strength of the electric dipole from the source of concentrated charge 204 (e.g., in C-m) and, E, is the strength of the received electric field (e.g., in V/m).

In many instances, the proof mass 202 responds to the torque by rotating about a torque axis (shown as axis $\tau$ in FIGS. 2A and 2B). In one example, the rotation can be represented as:

$$\theta = \tau/(Is^2) + (Ds) + k$$

where, $\theta$, is the angle of rotation, $\tau$, is the torque, I, is the polar moment of inertia, s, is the complex frequency, D, is a damping coefficient, and k is the rotational stiffness. In this way, the torque generated from the electric field induces motion in the proof mass 202, which reacts against the stiffness of the supports 206 (or the levitation suspension system 1000).

In various examples, the rotation of the proof mass 202 increases or decreases the distance between the proof mass 202 and the sense electrode(s) positioned on the substrate 222. As the distance between the proof mass 202 and the sense electrode(s) increases or decreases, the relative capacitance between the sense electrode(s) and the proof mass 202 varies. The resulting change in capacitance can be measured by the electronics to estimate the characteristics of the received electric field. In various examples, the electric field detector 200 may include a plurality of electrical leads 218, at least one of which couples a sense electrode to a corresponding contact 216. Each electrical contact 216 may connect the corresponding lead 218 to the control circuit, which may determine a direction (or directions), a magnitude, and/or a phase of the received electric field based on the sensed variation in capacitance. As illustrated, the substrate 222 may be coupled to the baseplate 214. Accordingly, the baseplate 214 supports the substrate 222, as well as other components of the detector 200, and may include one or more fasteners for creating a seal with the housing 210.

In certain examples, the control circuit may also send one or more control signals to the electrical contacts 216 and the corresponding leads 218. In particular, the control circuit may generate one or more control signals which can be used charge one or more drive electrodes and produce a feedback torque on the proof mass 202. That is, the electric field detector 200 may further include one or more drive electrodes positioned on the substrate 222 (e.g., within the substrate offset space) which rebalance the proof mass 202 to a nominal rotational position based on a received control signal. Such an arrangement may reduce non-linearities in the capacitance measurements (e.g., from the supports 206) while also extending the dynamic range of the electric field detector 200. In such an example, a lead 218 may receive the control signal from a contact 216 and provide the control signal to a drive electrode.

In certain examples, the electric field detector 200 may include a source of concentrated charge 204 (e.g., concentrated electrical charge). In the example shown in FIG. 2A, the source of concentrated charge 204 is coupled to a top surface of the proof mass 202; however, in certain other examples, the proof mass 202 itself may be composed of charge concentrated material. That is, a body of the proof mass 202 may be composed of a source of concentrated charge. In various examples, the source of concentrated charge 204 may include any suitable source of a semi-permanent static electric dipole, such as an electret or a capacitor plate having a residual free charge and/or polarization. As will be understood to one of ordinary skill in the art, the term "electret" refers to the dielectric equivalent of a permanent magnet.

For example, an electret configured for use in the detector 200 may be formed by: (a) applying heat to the electret material, (b) in response to obtaining a predetermined temperature, applying a voltage to the electret material, at which point the electret material will act like a capacitor and store the applied charge, and (c) cooling the electret material to a predetermined temperature. Thereafter, the electret maintains a residual charge after the field is removed. As an additional example, the electret material may be bombarded with radiation to generate a residual charge. Accordingly, real surface charges or aligned dipoles are immobilized in the bulk of the dielectric material.

Materials such as Polytetrafluoroethylene (PTFE), silicon nitride, Fluorinated Ethylene Propylene (FEP), a Perfluoroalkoxy alkane (PFA) material, Cyptop, Cylotene, and other dielectrics may be suitable materials that can be used as an electret. In certain examples the electret may include, but is not limited to, Thermo-electrets, MPEs (metal-polymer electrets), Radio-electrets, and Mechanoelectrets. In some examples, the source of concentrated charge 204 may be charged (i.e., applied a voltage) prior to coupling the source of concentrated charge 204 to the proof mass 202. In certain other examples, the source of concentrated charge 204 may be first coupled to the proof mass 202, and then charged. After formation, residual surface potentials can be maintained with no power input since the charge is retained in the source of concentrated charge 204 (e.g., in deep traps within the electret material). In some instances, the residual surface potential may be more than 1 kV.

Further examples of the source of concentrated charge 204 may include a series of two or more stacked electrets or a plurality of electrets arranged in a predetermined order. To increase the strength of the electric dipole, and therefore increase the sensitivity of the detector 200 to electric fields, micron-thick layers of electrets may be stacked together. Metal layers may be interposed between one or more layers of the source of concentrated charge 204 (e.g., stacked electret layers) to increase the gain of the one of more field concentrators 208 positioned adjacent the proof mass 202. For example, the metal layers of some embodiments may include layers of gold or platinum.

In other examples, the source of concentrated charge 204 may generate a semi-permanent dynamic electric dipole by driving a piezo-electric material (e.g., PZT). For instance, the control circuit may continuously, or periodically, drive the PZT to refresh the charge distribution when depleted. In other examples, the control circuit may actively generate a voltage gradient across the proof mass 202 of the electric field detector 200 to generate a dynamic electric dipole. In such an example, one or more electrodes or Piezo-electric materials may supply an induced voltage (e.g., active excitation signal) to vary a dynamic electric dipole at the proof mass 202. Specifically, the electrodes may be driven by the control circuit at an alternating-current (AC) frequency such that the detector 200 up-converts (e.g., increases a frequency) the received electric field information to a frequency above a 1/f noise limit, improving the performance of the detector 200.

As illustrated in at least FIGS. 2A-2B, in at least one example the proof mass 200, the supports 206, and the anchors 212a, 212b are defined in a same structure wafer. For instance, the structure wafer may include a Silicon-on-Insulator wafer having a flexure layer, a handle layer, and an oxide layer. The oxide layer may be interposed between the flexure layer and the handle layer. As further described with reference to FIGS. 7A-7C and FIGS. 8A-8C, the proof mass 202, the supports 206, and the anchors 212a, 212b may be defined in the flexure layer. It is appreciated that in some instances, the source of the concentrated charge 204 and/or an intervening material (e.g., a glue or other adhesive material) between the source of concentrated charge 204 and the proof mass 202 may introduce an asymmetry in a balance of the proof mass 202. Such an asymmetry may generate undesired sensitivities to external accelerations. In certain particular examples, the electric field detector 200 may include the one or more counterbalances, such as the counterbalance 226, to compensate for asymmetries.

In various examples, the electric field detector 200 may alternatively or additionally compensate for the external accelerations, and/or effects from other external parameters, by directly measuring the external parameter with an auxiliary sensor, and adjusting the measured electric field to compensate for the external parameter. For instance, in addition to external accelerations, the auxiliary sensor may measure at least one of noise, ambient temperature, or vibrations. Accordingly, the auxiliary sensor may be an accelerometer, temperature sensor, or noise sensor, to name a few examples. The control circuit may receive measurements from the auxiliary sensor use various filtering techniques (e.g., digital signal processing filter techniques), for example, to adjust the characteristic of the electric field to compensate for the effect(s) of the measured external parameter on the measured characteristic of the electric field. In various examples, adjusting the measured characteristic of the electric field may include applying a filter to remove the effect of the external parameter. The particular arrangement and position of auxiliary sensors within the electric field detector 200 may vary based on the particular external parameter desired to be measured, as well as, the particular architecture of the electric field detector 200 itself. Accordingly, an auxiliary sensor is generally represented by auxiliary sensor block 230 in FIG. 2A (removed in FIG. 2B and FIG. 3).

Figure 3:
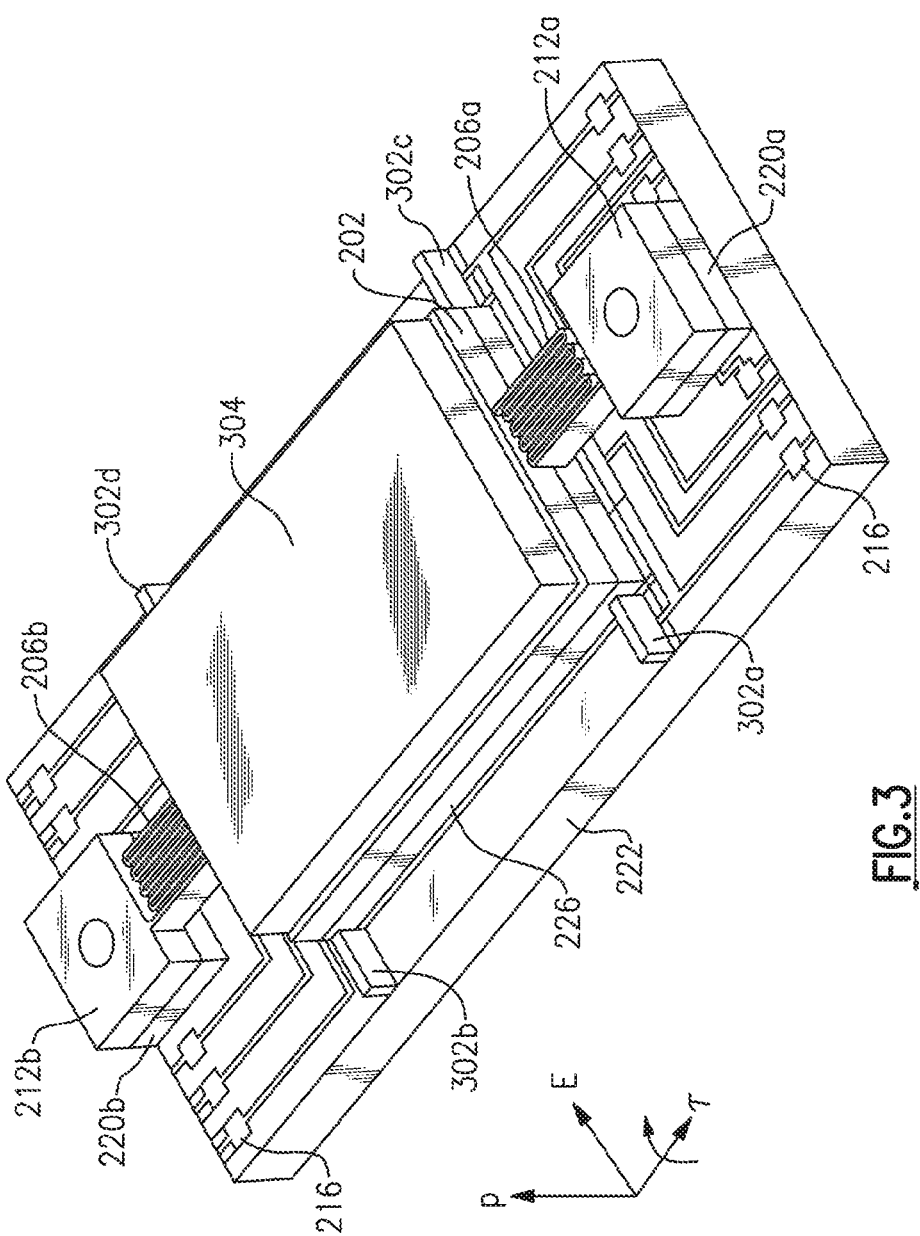
FIG. 3 is another perspective view of components of the electric field detector illustrated in FIG. 2A, according to examples discussed herein.

Referring to FIG. 3, there is illustrated a view of the electric field detector 200 shown in FIGS. 2A and 2B with at least the housing 210 and the baseplate 214 removed. In FIG. 3, a counterbalance 226 is positioned on a bottom surface of the proof mass 202 and also suspended above the substrate offset space. The counterbalance 226 reduces the pedulosity of the proof mass 202 and, therefore, a sensitivity of the proof mass 202 to undesired inputs, such as vibrations. In further examples, mechanical stops 302a, 302b, 302c, 302d may be coupled to the counterbalance 226 to prevent large excursions of the proof mass 202 from a predefined area of travel. That is, the mechanical stops 302a, 302b, 302c, 302d may be positioned to define a limit of travel of the proof mass 202 relative to the substrate 222 and within the detector 200. For example, FIG. 3 shows each of the mechanical stops 302a, 302b, 302c, 302d coupled to a side surface of the counterbalance 226. While shown as having one of the mechanical stops 302a, 302b, 302c, 302d at each corner of the rectangular counterbalance 226, in various other examples, the mechanical stops 302a, 302b, 302c, 302d may be positioned at other locations on the counterbalance 226, or may be attached to the housing 210.

Returning to FIGS. 2A and 2B, the flux concentrators 208 can operate to focus the received electric field on the source of concentrated charge 204. As shown, the flux concentrators 208 may be integrated within the housing 210, and in particular, attached to an interior surface of the housing 210. In other examples, the flux concentrators 208 may be attached to the substrate 222 or the baseplate 214. In various examples, the flux concentrators 208 magnify the intensity of the electric field near the location where the electric field intercepts the source of concentrated charge 204. The flux concentrators 208 may each be composed of metal, or a material with a high dielectric constant, which routes the flux through a spatial volume thereof. For example, each flux concentrator 208 may be composed of copper. By positioning the flux concentrators 208 near the source of concentrated charge 204, the electric field is concentrated to provide a gain at the source of concentrated charge 204. In the shown example, a first flux concentrator 208a is positioned proximate a side surface of the proof mass 202 and a second flux concentrator 208b is positioned proximate another, distal, side surface of the proof mass 202.

In various examples, each flux concentrator 208 is positioned as close as possible to the source of concentrated charge 204 to maximize the provided gain. The performance of each flux concentrator 208 may also be enhanced by increasing a length and/or an area of the respective flux concentrator 208 to maximize the amount of flux received and directed to the source of concentrated charge 204. Relative to the housing 210, each flux concentrator 208 may be internal, external, or a combination of both depending upon the level of enhancement desired. In addition to the flux concentrators 208, in certain examples the electric field detector 200 may include additional signal processing components which enhance the ability of the electric field detector 200 to resolve small signals. Such components are further described below with reference to at least FIG. 6. According to certain other examples, the one or more sense electrodes and the one or more drive electrodes that provide the capacitive readout may be replaced by other structures that are configured to measure the torque on the proof mass 202 from a received electric field. For instance, the electric field detector 200 may include one or more sensors that measure the torque by its effect on a frequency of one or more of the plurality of supports 206, or one or more sensors that optically measure a displacement of the proof mass 202.

As also shown in FIGS. 2A and 2B, in various examples the electric field detector 200 includes the housing 210. The housing 210 is positioned to encompass the other components of the electric field detector 200, such as the proof mass 202, the plurality of supports 206, the one or more flux concentrators 208, the one or more anchors 212, the substrate 222, the sense electrodes, the drive electrodes, and the one or more electrical contacts 216, among other components. In certain examples, the housing 210 may provide a vacuum environment which reduces the sensitivity of the electric field detector 200 to acoustic coupling and air damping, which reduces Brownian noise. A vacuum environment also helps to ensure that a minimal charge is maintained by preventing the dielectric breakdown of air within the electric field detector 200. In addition to these benefits, the housing 210 protects the discussed components of the electric field detector 200 from dust, moisture, and other contaminants. In one example the housing 210 may be formed from transparent glass to permit displacement of the proof mass 202 to be measured optically.

According to an example, a scale factor of the electric field detector 200 may be increased by using one or more bias voltages to create an electrostatic spring with a negative stiffness relative to the mechanical stiffness of the supports 206. A strong bias voltage on a sense electrode, drive electrode, and/or other electrodes positioned near the proof mass 202 and/or source of concentrated charge 204 generates a force (e.g., negative spring force) which is opposite of the mechanical spring force of the supports 206, and thereby decreases the overall stiffness of the MEMS structure. Accordingly, when summed, the negative stiffness reduces the total stiffness of the electric field detector 200 and increases the response of the proof mass 202 to a received electric field. Such an approach provides the benefit of increased performance without the loss of robustness, which would otherwise result if the stiffness of each of support 206 was mechanically reduced. While in certain examples the electric field detector 200 may include additional electronics to create a negative spring by force inputs (e.g., a control loop or a magnetic field), application of bias voltages to create an electrostatic spring provides the benefit of low-noise performance and reduced complexity.

Figure 4:
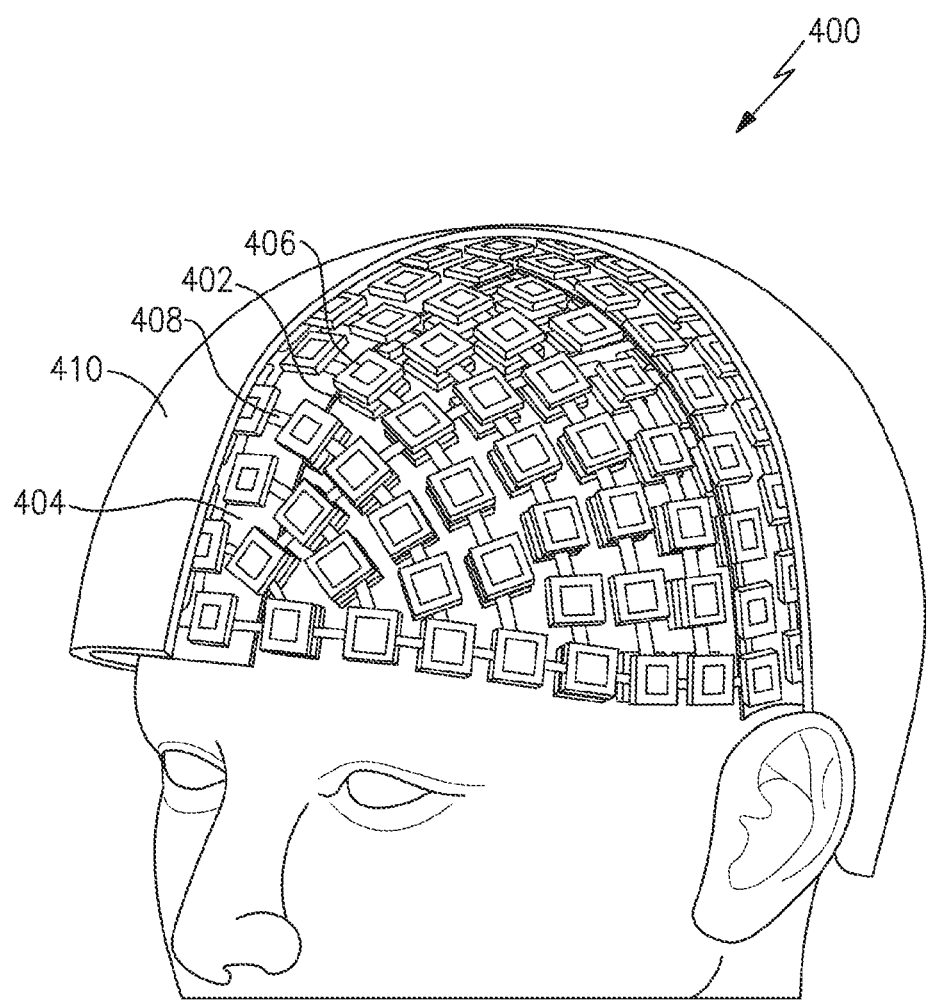
FIG. 4 is a perspective view of an array of electric field detectors incorporated within a headset, according to examples discussed herein.

As discussed herein, multiple electric field detectors 200 may be integrated into an array to enhance electric field detection performance. That is, an array of electric field detectors may be arranged to improve the ability of each individual detector to sense weak electric field signals and/or to measure a spatial distribution of electric fields around the user or patient. FIG. 4 shows one example of an array of electric field detectors incorporated within a headset 400. As shown, the headset 400 may be placed over the head of a patient, or user, to detect bio-electrical signals generated by the brain. It is appreciated that other implementations may be designed to detect bio-physical signals generated by other areas of the body of a patient or user, such as the heart, nerves, or muscles, to name a few examples.

In the example of FIG. 4, each electric field detector 402 within the array is coupled to the other electric field detectors 402 such that received electric field signals are coherently amplified while noise within the array remains incoherent. However, in certain other examples each electric field detector 402 may operate independently to individually measure the amplitude and phase of the received signal.

Referring to FIG. 4, each electric field detector 402 is located between a shield layer 404 (e.g., a faraday cage) and the scalp of the patient or user. Each electrical field detector 402 is closely spaced relative to the other electric field detectors 402 (e.g., approximately 1 cm apart) to maximize the spatial resolution of the array. On an opposite side of the shield 404 relative to the electric field detectors 402, additional electronics 406 can be positioned. Such an arrangement isolates the electric field detectors 402 from interfering effects which may arise from the operation of the additional electronics 406. For example, the additional electronics may include one or more auxiliary sensors, and/or circuitry for communicating with a control circuit, as discussed below. In this way, the shield 404 isolates the electric field detectors 402 from external noise sources (e.g., a 60 Hz power line noise), as well as, system components which may generate interference.

Each of the electric field detectors 402 and additional electronics 406 may be connected to a communication network via an electrical connection 408 that routes measured signals to a central location for processing. Auxiliary sensors may also be incorporated within the electronics 406 of the headset to measure effects which may introduce errors in the intended bio-electrical measurement (e.g., one or more external parameters). For example, inertial sensors and/or temperature sensors can be co-located with the electric field detectors 402 to measure electric fields, accelerations (e.g., patient movement), or temperature. Likewise, additional sensors, such as blink detectors or other physiological monitors can be incorporated within the headset 400 to improve the accuracy and performance of the array. As shown, components of the headset 400 are embedded within a cap 410 which provides structure and supports the various components. The cap 410 may include padding and other helmet features (e.g. aesthetically pleasing covers) to increase comfort and improve the user experience.

Accordingly, the array of electric field detectors may provide numerous benefits in various applications. For instance, the array may provide diagnostic information for educational applications, training applications, and cognitive enhancement applications. Moreover, current diagnostic techniques and approaches for neurological conditions may be enhanced by the information ascertained by the array of electric field detectors 402. For instance, the array of electric field detectors 402 enhances current techniques for treating ADHD, autism, dyslexia, depression, insomnia, impulsivity, and anxiety. Other relevant clinical applications include, but are not limited to, pain management, mental health treatment, epilepsy, and dementia, among other brain disorders.

Figure 5:
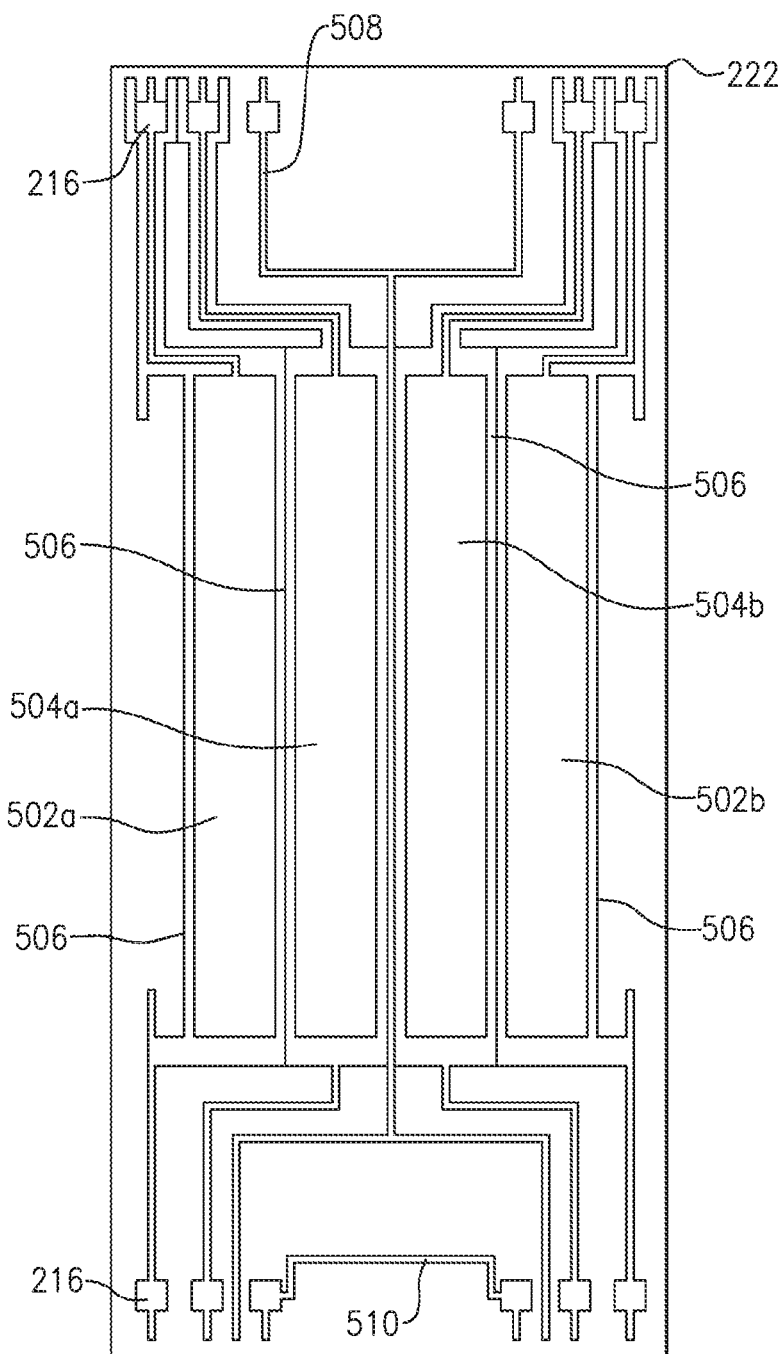
FIG. 5 is a plan view of the sense electrodes and drive electrodes of the electric field detector illustrated in FIG. 2A, according to examples discussed herein.

Referring now to FIG. 5, illustrated is a plan view of the sense electrodes 502a, 502b (collectively "sense electrodes 502") and drive electrodes 504a, 504b (collectively "sense electrodes 504") of the electric field detector 200 illustrated in FIGS. 2A and 2B. In particular, FIG. 5 illustrates the electrical connections between the sense electrodes 502 and the corresponding electrical contacts 216, and the electrical connections between the drive electrodes 504 and the corresponding electrical contacts 216. As previously discussed, leads 118 may couple electrical contacts 216 on the substrate 122 and electrical contacts 216 on the baseplate 114 to the control circuit. For the convenience of illustration, leads 218 are not shown in FIG. 5. As discussed above with reference to FIGS. 2A and 2B, in various examples the sense electrodes 502 and the drive electrodes 504 are formed on the substrate 222, and in particular, within the substrate offset space beneath the proof mass 202. FIG. 5 is described with continuing reference to the electric field detector 200 illustrated in FIGS. 2A and 2B, and the components thereof.

FIG. 5 illustrates a first sense electrode 502a (e.g., a left sense electrode), a second sense electrode 502b (e.g., a right sense electrode), a first drive electrode 504a (e.g., a left torquer), and a second drive electrode 504b (e.g., a right torquer). As further discussed with reference to FIGS. 7A-7C and FIGS. 8A-8C, each of the first sense electrode 502a, second sense electrode 502b, first drive electrode 504a, second drive electrode 504b, and electrical contacts 216 may be applied as a metallization layer to the substrate 222. For instance, each sense electrode 502, each drive electrode 502, and/or each electrical contact 216 may be a layer of chrome, platinum, or gold on the substrate 222. As previously described, one or both of the sense electrodes 502 may be used to measure a change in capacitance (e.g., electrical capacitance) relative to the proof mass 202 as a result of torsional movement of the proof mass 202. One or both of the drive electrodes 504 may be used to produce a feedback torque on the proof mass 202 and reposition the proof mass 202.

In one example, the two sense electrodes 502a, 502b are used for a differential capacitance measurement, and the two drive electrodes 504a, 504b are used as torquers for force feedback during closed loop operation. Each sense electrode 502 and drive electrode 504 is interposed between a pair of respective electrical contacts 216 and extended along a length of the substrate 222. While shown in FIG. 5 as a pair of sense electrode plates and a pair of drive electrode plates, each plate having a substantially rectangular shape, in various other examples any suitable number of sense electrodes 502 and drive electrode 504 may be used, and each of the sense electrodes 502 or drive electrodes 504 may have any suitable shape. Moreover, in certain examples the first sense electrode 502a and the first drive electrode 504a may be connected and act as a single large electrode to maximize performance when not operating in a closed loop mode of operation. In such an example, the second sense electrode 502b and the second drive electrode 504b may be coupled in a similar manner. In certain examples, the sense electrodes 502 and the drive electrode 504 may be reversed and their relative areas chosen to optimize the relative level of performance between the drive and sense operations. In one example, the sense electrodes 502a, 502b (e.g., the outer positioned electrodes) act on the plurality of supports 206 of the detector 200, and therefore may have a greater effectiveness.

In various examples, each sense electrode 502 and drive electrode 504 may include a respective guard ring 506. As shown in FIG. 5, the proof mass 202 may also have a guard ring 508. Each guard ring 506 substantially surrounds the respective sense electrode or drive electrode and separates that sense electrode or drive electrode from the other sense electrode and drive electrode. In one example, each the guard ring 506 is a thin metal track that traces the perimeter of the corresponding plate or electrode. Each guard ring 506, 508 substantially eliminates direct-current (DC) current and low-frequency leakage currents from unintentionally effecting the corresponding sense electrodes 502, drive electrodes 504, or proof mass 202. DC current and low-frequency leakage current may limit the dynamic range of the electric field detector 200 and may create low-frequency noise by producing undesired voltages in the source impedances. FIG. 5 further shows a ground contact 510 for the proof mass 202.

Figure 6:
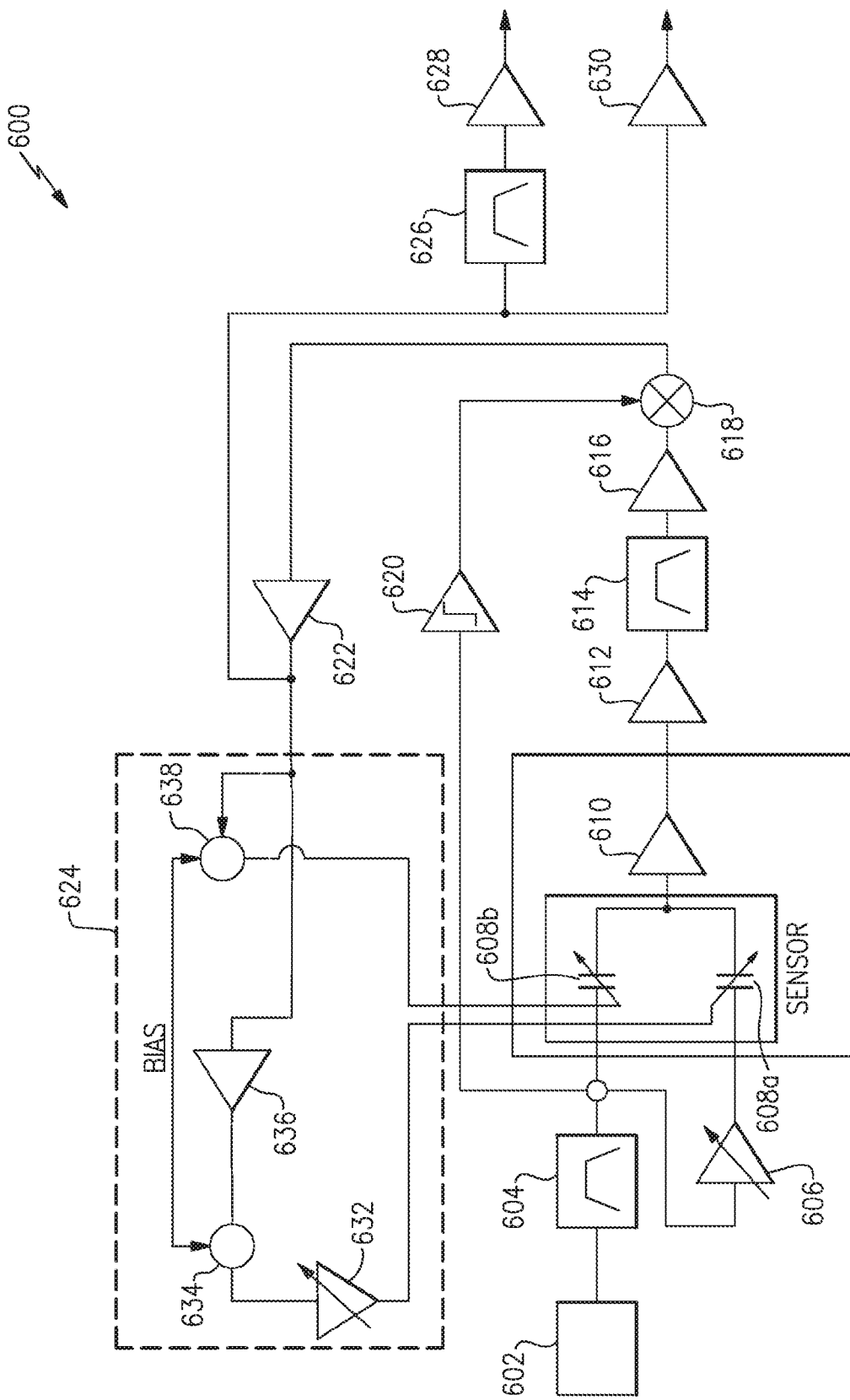
FIG. 6 is a block diagram of a control circuit according to examples discussed herein.

Turning now to FIG. 6, shown is one example of a control circuit 600 that may be coupled to the electric field detector 200 illustrated in FIGS. 2A and 2B to detect the characteristics of an electric field received at the detector 200 and/or provide one or more control signals (e.g., for driving the drive electrodes). For instance, the control circuit may be coupled to the contacts 216 illustrated in FIGS. 2A and 2B. FIG. 6 is discussed with continuing reference to the electric field detector 200 of FIGS. 2A and 2B, and the components thereof.

In certain examples, the control circuit 600 may include any processor, multiprocessor, or controller. The processor may be connected to a memory and a data storage element. The memory stores a sequence of instructions coded to be executable by the processor to perform or instruct the various components discussed herein to perform the various processes and acts described herein. For instance, the control circuit 600 may communicate with, and provide one or more control signals to the sense electrodes and the drive electrodes of the electric filed detector via the contacts 216 and the leads 218. The memory may be a relatively high performance, volatile random access memory such as a dynamic random access memory (DRAM) or static memory (SRAM). However the memory may include any device for storing data, such as a disk drive or other nonvolatile storage device.

The instructions stored on the data storage may include executable programs or other code that can be executed by the processor. The instructions may be persistently stored as encoded signals, and the instructions may cause the processor to perform the functions and processes described herein, such as providing one or more control signals to generate a feedback torque. The data storage may include information that is recorded, on or in, the medium, and this information may be processed by the processor during execution of instructions. The data storage includes a computer readable and writeable nonvolatile data storage medium configured to store non-transitory instructions and data. In addition, the data storage includes processor memory that stores data during operation of the processor.

In the illustrated example, the control circuit 600 includes a precision square-wave generator 602 which is coupled to a first filter 604. The precision square-wave generator 602 generates a signal which is converted to a sine wave by the first filter 604. The first filter 604 may include any suitable filter designed to accept a square-wave input and provide a sinusoidal output. For instance, one example is a low-Q active bandpass filter with a notch filter to reduce the third-order harmonic. In various examples, the first filter 604 has a very low amplitude sensitivity to temperature, such as 1-3 ppm per degree Celsius. The first filter 604 is coupled to an inverting amplifier 606 which has an adjustable gain and a nominal gain of −1. Accordingly, an output of the first filter 604 and the inverting amplifier 606 form a low-noise differential sine-wave carrier generator.

As shown in FIG. 6, the carrier generator may be coupled to each of the sense electrodes (e.g., shown as readout capacitors 608a, 608b, collectively "readout capacitors 608") to excite the readout capacitors 608 in order to up-convert (e.g., increase a frequency) an electronics signal produced by the received electric field. In various examples, by up-converting the received electric field information, the information is converted to a frequency where amplifier noise is significantly lower. Moreover, the up-conversion reduces the sensitivity of the electric field to current noise sources in a preamplifier 610 coupled to the readout capacitors 608. While not illustrated in FIG. 6, in many instances the control circuit 600 may include one or more passive high-pass filters interposed between the outputs of the carrier generator and the readout capacitors 608 to reduce low-frequency voltage noise coupled to the readout capacitors 608 from the carrier generator. Such an arrangement offers the benefit of reduced low-frequency torque noise.

Referring to the electric field detector 200 of FIG. 2A, in the absence of an electric field, there will be no torque on the proof mass 202 (in an ideal case). In such a situation, no electric field information is passed from the readout capacitors 608 (sense electrodes 502 in FIG. 5) to the preamplifier 610. However, when an electric field is present, the readout capacitors 608 provide a measured signal to the preamplifier 610, which in turn provides an output of a carrier signal amplitude-modulated by the electric field (e.g., a double-sideband suppressed carrier signal).

In various examples, the control circuit 600 includes a second amplifier 612 and a second filter 614 coupled to the output of the preamplifier 610. For instance, the second amplifier 612 may include a low-noise instrumentation amplifier with an input-referred noise density that is substantially less than the output-referred noise density. The carrier signal amplitude-modulated by the electric field is received and amplified by the second amplifier 612 before being filtered by the second filter 614 and received at a demodulator 618. According to certain examples, the second filter 614 includes a band-pass filter which has a low quality factor to reduce the noise within the amplitude-modulated carrier signal at the third order and higher order harmonics.

Accordingly, the second filter 614 provides filtering functionality to prevent higher order harmonics from affecting the noise performance of the control circuit 600 after the carrier signal has been demodulated. In certain implementations, the control circuit 600 may also include a third amplifier 616 which is coupled to an output of the second filter 614 and configured to add an additional gain to the carrier signal amplitude-modulated by the electric field information. While illustrated in FIG. 6 as separated from the second filter 614, in certain examples the third amplifier 616 provides additional AC gain and may be incorporated into the second filter 614.

As shown in FIG. 6, the control circuit 600 includes a demodulator 618 and comparator 620 which are coupled to form a switching (or square-wave) demodulator. In FIG. 6, the switching demodulator is coupled to an output of the third amplifier 616. The demodulator 618 drives a controller 622, which is coupled to the output of the demodulator 618. In some examples, the controller 622 may include an Integral-Derivative (ID) controller, a Proportional-Integral-Derivative (PID) controller, or any other suitable predictive controller. In one example, the controller 622 drives a torque generator 624 which produces a bias voltage at each respective torque generator electrode (e.g., drive electrodes 504a, 504b illustrated in FIG. 5). In particular, the torque generator may produce respective torque generator voltages of (BIAS+K*$V_C$) and (BIAS−K*$V_C$), where "BIAS" is a bias voltage, "K" is a scaling constant, and "$V_C$" is the output of the controller 622. For example, the torque generator 624 may produce a substantially constant bias voltage having a nominal value near one-half of the positive or negative supply voltage. While in the illustrated example, the torque generator 624 includes summation blocks 634, 638, an inverting gain 636, and an adjustable gain 632 for the purpose of illustration, in various other examples the torque generator 624 may be implemented with various other suitable components.

Accordingly, the applied torque, which is proportional to the square of the voltage, is directly proportional to the output of the controller 622. Such a biasing arrangement achieves a linearization of the closed-loop feedback torque applied to the proof mass 202 with respect to the output of the controller 622. This arrangement results in a linear control loop and permits a linear readout of the electric field information. In certain examples, the control circuit 600 may further include one or more passive low-pass filters (not shown) interposed between the torque generator 624 and the torque generator electrodes in order to reduce carrier-band noise applied to the torque generator electrodes.

As further illustrated in FIG. 6, the control circuit 600 may include a baseband filter 626 coupled to the output of the controller 622. For example, the baseband filter 626 may include a bandpass filter having a passband selected to extract the electric field information within the desired bandwidth from the output of the demodulator 618. The output of the baseband filter 626 may then be amplified by a fourth amplifier 628 and provided to an output of the control circuit 600 or one or more downstream diagnostic electronics. In at least one example, the fourth amplifier 628 is designed such that most of a variable voltage range of the amplifier 628 corresponds to a maximum expected in-band field strength of the electric field. Such a design provides the benefit of reduced noise. For instance, the fourth amplifier 628 may include a high-gain amplifier that has a gain of about 100. The parameters of the fourth amplifier 628 may be selected in conjunction with the parameters of the baseband filter 626 to select and amplify a desired frequency band (e.g., a frequency band associated with brain activity (0.5 Hz-100 Hz)). As shown, in certain examples the control circuit 600 may also include a fifth amplifier 630 to provide an unfiltered output for diagnostic purposes.

Though the features within FIG. 6 are illustrated as blocks within a block diagram, unless otherwise indicated, the features may be implemented as signal processing circuitry, and may be implemented with one or more specialized hardware components or one or more specialized software components. For instance, the control circuit 600 may be implemented as one of, or a combination of, analog circuitry or digital circuitry. The control circuit 600 may be composed of an array of logic blocks arranged to perform one or more of the corresponding signal processing operations described herein. In particular, the processing circuitry may implemented by an array of transistors arranged in an integrated circuit that provides a performance and power consumption similar to an ASIC (application-specific integrated circuit) or an FPGA (field-programmable gate array). In other examples, components of the control circuit 600 may be implemented as one or more microprocessors executing software instructions (e.g., predefined routines). In particular, the software instructions may include digital signal processing (DSP) instructions. Unless otherwise indicated, signal lines may be implemented as discrete analog or digital signal lines, or as a single discrete digital signal line with appropriate signal processing to process separate signals.

Figure 7C:
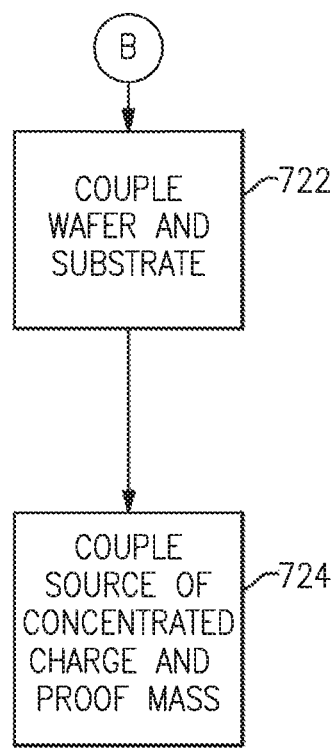
Figure 8C:
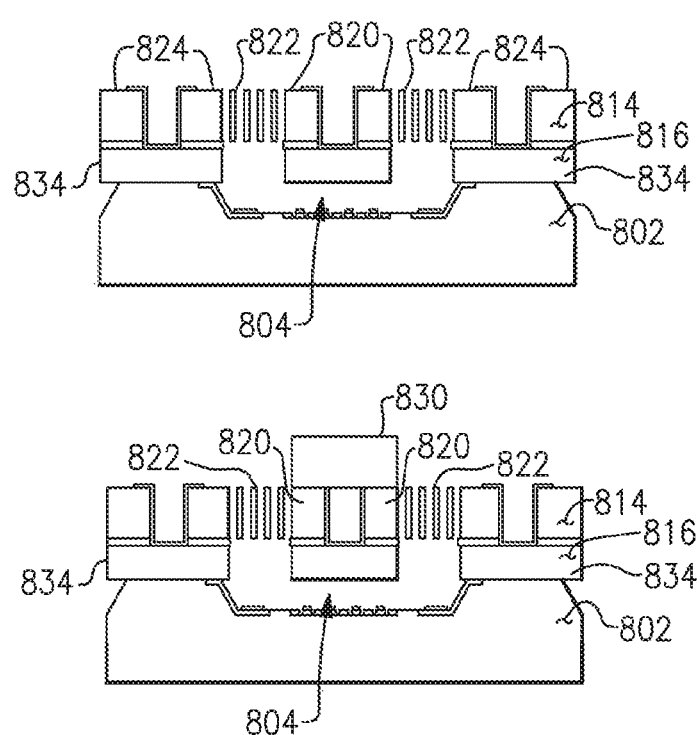

Turning now to FIGS. 7A-7C and FIGS. 8A-C, illustrated is an example of a process 700 for fabricating an electric field detector, such as the electric field detector 200 illustrated in FIGS. 2A-2B and FIG. 3. In particular, FIG. 7A-7C illustrates the process flow and FIGS. 8A-8C show a state of an electric field detector during each act of the process 700. Each act of the process 700 of FIG. 7A-7C is illustrated immediately adjacent the corresponding state of production of the electric field detector. Accordingly, in some examples, the electric field detector shown in FIGS. 8A-8C may be one implementation of the electric field detector 200 described with reference to at least FIGS. 2A and 2B. That is, at least the source of concentrated charge, the substrate, the support(s), the proof mass, the sense electrode(s), and the drive electrode(s) described with reference to FIGS. 8A-8C may correspond to the source of concentrated charge, the substrate, the support(s), the proof mass, the sense electrode(s), and the drive electrode(s) previously described with reference to at least FIGS. 2A and 2B, as well as, the sense electrode(s) and the drive electrode(s) described with reference to FIG. 5.

The process 700 begins at act 702 which may include the act of providing a substrate wafer 802 (referred to generally as the "substrate 802"). In various examples, the substrate 802 is a glass wafer. The glass wafer may be doped such that it conducts electricity at elevated temperatures (e.g., about 350 degrees Celsius). The glass wafer may be composed of borosilicate, for example. In act 704, the process 700 includes defining a well 804 (e.g., a substrate offset space) in the substrate 802. In certain examples, the substrate offset space is formed by etching the substrate 802; however, other processing techniques may be used, such as milling, grinding, or one or more deposition processes. For instance, the etching process may be implemented using the MESA™ etch system offered by APPLIED MATERIALS™ of Santa Clara, Calif. Areas of the substrate 802 which are not etched during act 704 may be later coupled to a flexure layer 814 or a handle layer 816 of a structure wafer 812, as discussed below.

In act 706, the process 700 may include depositing a conducting material, such as metal, on the substrate 802 to form one or more sense electrodes 806, one or more drive electrodes 808, and/or one or more guard rings and electrical contacts (not shown). In the shown example, the conducting material is primarily deposited within the substrate offset space 804. For instance, each sense electrode 806 and each drive electrode 808 may be formed on a surface of the substrate 802 within the substrate offset space 804. As discussed with reference to FIGS. 2A and 2B, each sense electrode 806 may be configured to measure a change in capacitance within the substrate offset space 804 (e.g., between the sense electrode and a proof mass), and each drive electrode 808 may be configured to act as a closed loop torquer on the proof mass. Each guard ring is formed on the substrate 802 to substantially surround a corresponding one of the sense electrodes 806 or drive electrodes 808 and isolate that respective sense or drive electrode plate 806, 808 from the effects of direct-current (DC) current and low-frequency leakage currents.

In act 708, the process 700 may include conditioning the surface(s) of one or more sense electrodes 806 and/or drive electrodes 808 to increase the surface texture thereof. In one example, act 708 may include applying one or more small metal bumps 810 to the surface of the sense electrodes 806 and/or drive electrodes 808. The increase in surface texture decreases the holding force between the substrate 802 and the structure wafer 812 by reducing the contact area between the substrate 802 and the structure wafer 812.

In act 710, the process 700 may include providing a structure wafer 812, such as a Silicon-on-Insulator (SOI) wafer. While a SOI wafer is used as one example for the purpose of explanation, in various other examples other suitable structure wafer materials may be used, such as quartz, polysilicon, etc. In the shown example of FIGS. 8A-8C, the structure wafer 812 includes a flexure layer 814 and a handle layer 816 separated by a buried oxide layer 818. In one example, the flexure layer 814 is about 400 μm thick (e.g., ±2 μm thickness), the handle layer 816 is about 300 μm thick (e.g., ±2 μm thickness), and the buried oxide 818 is about 2 μm thick (e.g., ±1 μm thickness).

Referring to FIG. 7B and FIG. 8B, in act 712 the process 700 may include defining a proof mass 820, a plurality of supports 822, and/or one or more anchors 824 in the structure wafer 812. In the shown example of FIG. 8B, each support 822 is interposed between the proof mass 820 and a respective anchor 824. In certain examples, the proof mass 820, the plurality of supports 822, and/or one or more anchors 824 are formed by etching the flexure layer 814 of the structure wafer 812; however, other processing techniques may be used, such as milling, grinding, or one or more deposition processes. In certain examples, a Deep Reactive Ion Etch (DRIE) process may be used with a dry etch tool and Inductively Coupled Plasma (ICP) to define each of the proof mass 820, supports 822, and the anchors 824. In one example, the ICP etch may also define one or more holes in the flexure layer 814. Each hole may be used to electrically connect the flexure layer 814 and the handle layer 816, as described during later processing acts of FIG. 7A-7C. In FIG. 7B, the flexure layer 814 is shown as having a hole 832a within the proof mass 820 and a hole 832b, 832c within each anchor 824.

In act 714, the process 700 may include selectively removing a first portion of the oxide layer 818 from the structure wafer 812. In particular, the first portion may include those areas of the oxide layer 818 that were exposed during the etching process of act 712. That is, in one example act 714 may include removing the exposed oxide from the holes 832a, 832b, 832c in the flexure layer 814. For instance, an oxide ICP etch may be used to remove the exposed oxide. Following act 714, in act 716 the process 700 may include defining one or more counterbalances in the handle layer 816 of the structure wafer 812. For instance, act 716 may include etching the handle layer 816 to define a counterbalance 826 for the proof mass 820. In act 716, the process 700 may further include defining one or more anchor grounds 834. Each anchor ground 834 couples a respective anchor 824 to the substrate 802, as further discussed below with reference to act 722.

In act 718, the process 700 may include selectively metallizing each recess formed in the flexure layer 814 of the structure wafer 812 to plate the one or more formed recesses. The deposited metal 828 forms an electrical connection between the flexure layer 814 and the handle layer 816. Following act 718, in act 720 the process 700 includes the act of etching a second portion of the oxide layer 818. As shown in FIG. 8B, the second portion of the oxide layer 818 may include those sections of the oxide layer 818 that are attached to the supports 822. Accordingly, act 720 may include releasing the supports 822 from the oxide layer 818 to suspend the proof mass 820. In at least one example, the supports 822 are released by removing the second portion of the oxide layer 818 using a Hydrofluoric acid (HF) etching process.

Once each of the supports 822 has been released, the process 700 may include coupling the structure wafer 812 to the substrate 802, as shown in FIG. 8C. In one example, the handle wafer 816 may be anodically bonded to the substrate 802. Once the structure wafer 812 has been coupled to the substrate 802, the proof mass 820 may be suspended above and partially within the substrate offset space 804 by the plurality of supports 822. The anchor grounds 834 may couple the flexure layer 814 to the substrate 802 at each end of the flexure layer 814 (e.g., at each anchor 824), where the substrate offset space 804 is substantially in the center of the substrate 802. In an example where multiple electric field detectors are fabricated from the same of substrate 802 material and structure wafer 812 (e.g., SOI wafer), the process 700 may then include dicing each sheet to separate each of the separate electric field detectors. The process 700 ends in act 724, in which a source of concentrated charge 830 is coupled to the structure wafer 812, and in particular, coupled to the proof mass 820. As shown, the source of concentrated charge 830 is positioned at about the center of the flexure layer 814 such that each of the supports 822 suspends the source of concentrated charge 830 above the substrate offset space 804. As discussed above, the source of concentrated charge 830 may be polarized before or after it has been coupled to the flexure layer 814. Processes and acts for operating the electric field detector once it has been fabricated are discussed above with reference to the electric field detector 200 shown in FIGS. 2A, 2B, and 3.

As discussed above, in various examples the assembled electric field detector may be packed with a housing, a baseplate, and one or more electrical connections, such as the housing 210 and the baseplate 214 illustrated in FIGS. 2A and 2B and the electrical connections illustrated in FIG. 5. In various examples, the source of concentrated charge 830 may be coupled to the flexure layer 814 early in the packaging process (e.g., before the sense electrodes 806 and/or drive electrodes 808 are electrically bonded to the substrate 802). However, in other examples, the source of concentrated charge 830 may be coupled to the flexure layer 814 as part of a vacuum sealing process with the housing, after integration in a sensor array, or during operation. In one particular example, an uncharged electret is attached to the flexure layer 814 and subsequently charged as part of a vacuum sealing process. For instance, once the detector is placed in the vacuum, an electron beam source may embed a charge on one or more surfaces of the uncharged electret to generate an electric dipole. The housing may then be attached to the baseplate of the detector to form a hermetic seal. Such a process provides the benefit of reducing air damping during operation of the detector. In other examples, charge can also be added after the housing is attached to form a hermetic seal, or continuously during operation, as is the case of an active system, where a voltage excitation is used to form an AC electric dipole on the proof mass.

As such, in addition to providing improved electric field detectors that exploit the electric component of electromagnetic signals, various other aspects and examples discussed herein provide improved fabrication processes for efficiently and cost-effectively producing a compact electric field detector. Particular examples of the electric field detector may include an electric field detector capable of detecting bio-physical signals generated by the body of a patient or user, such as the electric field of his or her brain, heart, nerves or muscles. When compared to available electromagnetic sensors examples of the electric field detector herein achieve a low noise (e.g., less than 1 mV/m/rtHz at 10 Hz) at a compact size (e.g., less than 1 cm$^3$) and a low production cost.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. An electric field detector comprising:
    a proof mass;
    a source of concentrated charge coupled to the proof mass;
    a substrate having a substrate offset space defined therein, wherein the proof mass is suspended above the substrate offset space;
    a first sense electrode disposed on the substrate within the substrate offset space and positioned proximate the proof mass, the first sense electrode being configured to measure a change in capacitance relative to the proof mass from torsional movement of the proof mass in response to a received electric field at the source of concentrated charge; and
    a control circuit coupled to the first sense electrode and configured to determine a characteristic of the electric field based on the measured change in capacitance, the control circuit including a preamplifier, a demodulator, and a baseband filter, the preamplifier being configured to provide a carrier signal amplitude-modulated by the electric field, the demodulator being configured to receive the amplitude-modulated carrier signal, and the baseband filter being configured to extract the characteristic of the electric field from an output of the demodulator.

2. The electric field detector of claim 1, further comprising a counterbalance coupled to the proof mass, wherein the source of concentrated charge is coupled to a first surface of the proof mass and the counterbalance is coupled to a second distal surface of the proof mass.

3. The electric field detector of claim 1, further comprising a second sense electrode coupled to the control circuit, wherein the second sense electrode is disposed on the substrate, and wherein the first sense electrode and the second sense electrode are configured to provide a differential capacitance measurement based on the change in capacitance from torsional movement of the proof mass.

4. The electric field detector of claim 1, further comprising at least one drive electrode coupled to the control circuit and positioned proximate the proof mass, wherein the at least one drive electrode is configured to produce a feedback torque on the proof mass.

5. The electric field detector of claim 4, wherein the at least one drive electrode is positioned on the substrate and within the substrate offset space.

6. The electric field detector of claim 5, further comprising a plurality of guard rings, each guard ring positioned to substantially surround a corresponding one of the first sense electrode or the at least one drive electrode.

7. The electric field detector of claim 1, wherein the source of concentrated charge is an electret.

8. The electric field detector of claim 1, further comprising at least one support coupled to the proof mass and configured to suspend the proof mass above the substrate offset space.

9. The electric field detector of claim 8, further comprising a structure wafer, wherein at least the proof mass and the at least one support are defined in the structure wafer.

10. The electric field detector of claim 9, wherein the structure wafer is a Silicon-on-Insulator (SOI) wafer having a flexure layer, a handle layer, and an oxide layer, the oxide layer being interposed between the flexure layer and the handle layer, and wherein the proof mass and the at least one support are defined in the flexure layer.

11. The electric field detector of claim 1, further comprising a levitation suspension system configured to levitate the proof mass relative to the substrate.

12. The electric field detector of claim 11, wherein the levitation suspension system includes at least one levitation forcer positioned proximate the proof mass and configured to apply a force to maintain the proof mass at a null point, and wherein the at least one levitation forcer is an electrostatic forcer or a magnetic forcer.

13. The electric field detector of claim 1, further comprising an auxiliary sensor coupled to the control circuit and configured to measure an external parameter, the external parameter including at least one of noise, a vibration, and an ambient temperature, and wherein the control circuit is configured to adjust the characteristic of the electric field to compensate for an effect of the measured external parameter on the characteristic of the electric field.

14. The electric field detector of claim 1, wherein the control circuit is further configured to apply a bias voltage and create a negative spring force on the proof mass.

15. An electric field transduction method comprising:
    generating an electric charge distribution on a proof mass, the proof mass being suspended above a substrate offset space in a substrate relative to a first sense electrode disposed on the substrate, the proof mass and at least one support suspending the proof mass above the substrate offset space being defined in a structure wafer including a flexure layer, a handle layer and a metallic layer disposed in one or more holes defined in the flexure layer electrically coupling the flexure layer and the handle layer;
    measuring a change in capacitance between the first sense electrode and the proof mass from torsional movement of the proof mass in response to receiving an electric field at the proof mass; and determining a characteristic of the electric field based on the measured change in capacitance.

16. The method of claim 15, further comprising providing a differential capacitance measurement from the first sense electrode and a second sense electrode based on the change in capacitance from the torsional movement of the proof mass.

17. The method of claim 16, further comprising suspending the proof mass relative to the first sense electrode with at least one of one or more supports, one or more rotational bearings, an electrostatic suspension, or a magnetic suspension.

18. The method of claim 15, further comprising providing a feedback torque on the proof mass with one or more drive electrodes positioned proximate the proof mass.

19. The method of claim 15, wherein generating the electric charge distribution on the proof mass includes forming a static electric dipole with an electret.

20. A method for fabricating an electric field detector comprising:

defining at least one substrate offset space in a substrate wafer;

forming a first sense electrode on the substrate wafer and within the substrate offset space;

providing a structure wafer, wherein the structure wafer includes a flexure layer and a handle layer;

applying a metallic layer to one or more holes defined in the flexure layer to electrically couple the flexure layer and the handle layer of the structure wafer;

defining a proof mass and at least one support in the structure wafer and suspending the proof mass by the at least one support to allow torsional movement of the proof mass;

providing a source of concentrated charge on the proof mass; and coupling the substrate wafer and the structure wafer to position the proof mass proximate the substrate offset space of the substrate wafer and within capacitive communication with at least the first sense electrode.

21. The method of claim 20, further comprising providing the structure wafer, wherein the structure wafer includes a flexure layer, a handle layer, and an oxide layer, the oxide layer being interposed between the flexure layer and the handle layer, and wherein defining the proof mass and the at least one support in the structure wafer includes etching the flexure layer to form the proof mass and the at least one support.

22. The method of claim 20, further comprising forming a second sense electrode, a first drive electrode, and a second drive electrode on the substrate wafer and within the substrate offset space.

* * * * *